United States Patent
Yuyama et al.

(10) Patent No.: US 9,493,290 B2
(45) Date of Patent: Nov. 15, 2016

(54) TABLET DISPENSER

(71) Applicant: YUYAMA MFG. CO., LTD., Toyonaka-shi, Osaka (JP)

(72) Inventors: Shoji Yuyama, Toyonaka (JP); Naoki Koike, Toyonaka (JP); Takafumi Imai, Toyonaka (JP); Yoshinori Kumano, Toyonaka (JP); Akira Maeda, Toyonaka (JP); Mitsuhiro Mitani, Toyonaka (JP)

(73) Assignee: YUYAMA MFG. CO., LTD., Toyonaka-shi (JP)

( * ) Notice: Subject to any disclaimer, the term of this patent is extended or adjusted under 35 U.S.C. 154(b) by 0 days.

(21) Appl. No.: 14/133,624

(22) Filed: Dec. 18, 2013

(65) Prior Publication Data

US 2014/0103063 A1  Apr. 17, 2014

Related U.S. Application Data

(63) Continuation-in-part of application No. 13/018,564, filed on Feb. 1, 2011, now Pat. No. 8,579,153, which is a continuation-in-part of application No. PCT/JP2009/006195, filed on Nov. 18, 2009.

(30) Foreign Application Priority Data

Nov. 21, 2008 (JP) .................................. 2008-298122
Mar. 2, 2009 (JP) .................................. 2009-048442
Aug. 24, 2009 (JP) .................................. 2009-193142

(51) Int. Cl.
*B65H 3/44* (2006.01)
*B65D 83/04* (2006.01)
*G07F 11/18* (2006.01)
*G07F 11/62* (2006.01)
*G07F 17/00* (2006.01)
*G06F 19/00* (2011.01)

(52) U.S. Cl.
CPC ............... *B65D 83/04* (2013.01); *G07F 11/18* (2013.01); *G07F 11/62* (2013.01); *G07F 17/0092* (2013.01); *G06F 19/3462* (2013.01)

(58) Field of Classification Search
CPC ..................... G07F 11/18; G07F 11/62; G07F 17/0092; B65D 83/04; G06F 19/3462
USPC .......... 700/231, 244, 243; 53/493, 508, 411; 364/479.01; 221/220, 202, 234, 178, 221/130
See application file for complete search history.

(56) References Cited

U.S. PATENT DOCUMENTS 3,385,085 A * 5/1968 Engel .............................. 68/18 F
4,551,024 A * 11/1985 Clapp ................... B28C 9/0463
 366/347
4,619,379 A * 10/1986 Biehl ........................ 222/153.14

(Continued)

*Primary Examiner* — Rakesh Kumar
(74) *Attorney, Agent, or Firm* — Masuvalley & Partners

(57) ABSTRACT

A tablet dispenser includes a device body and a plurality of tablet cassettes disposed on one face of the device body. Each tablet cassette is capable of accommodating a plurality of types of tablets and of dispensing the tablets contained therein in a lateral direction. A plurality of chutes are in communication with the plurality of tablet cassettes. Each chute is disposed on the one face of the device body, adjacent to a corresponding tablet cassette. Each chute retains tablets dispensed from the corresponding tablet cassette and dispenses the tablets in a downward direction into a container.

11 Claims, 30 Drawing Sheets

(56) References Cited

U.S. PATENT DOCUMENTS

| | | | | |
|---|---|---|---|---|
| 5,354,127 | A * | 10/1994 | Del Zotto | B01F 7/087 366/186 |
| 5,709,063 | A * | 1/1998 | Yuyama | B65B 1/06 53/154 |
| 5,787,678 | A * | 8/1998 | Koike | B65B 39/002 221/124 |
| 6,349,848 | B1 * | 2/2002 | Uema | G07F 17/0092 221/124 |
| 6,497,339 | B1 * | 12/2002 | Geltser | A61J 7/02 198/766 |
| 6,554,157 | B2 * | 4/2003 | Geltser | A61J 7/02 221/200 |
| 6,928,790 | B2 * | 8/2005 | Takahashi | B65B 5/103 221/251 |
| 7,174,693 | B2 * | 2/2007 | Wooldridge | 53/55 |
| RE40,453 | E * | 8/2008 | Lasher | G07F 5/18 221/174 |
| 7,412,302 | B2 * | 8/2008 | Cobb | G07F 17/0092 700/231 |
| 7,455,163 | B2 * | 11/2008 | Yuyama | B65B 35/04 193/2 R |
| 7,747,345 | B2 * | 6/2010 | Ohmura | G06F 19/3462 700/231 |
| 7,861,492 | B2 * | 1/2011 | Yuyama | B65B 5/103 221/2 |
| 8,061,560 | B2 * | 11/2011 | Farnsworth | B65B 39/001 221/234 |
| 8,141,330 | B2 * | 3/2012 | Henkel | B65B 5/103 53/237 |
| 8,146,777 | B2 * | 4/2012 | Inamura | 221/65 |
| 8,172,112 | B2 * | 5/2012 | Karwacki, Jr. | 222/181.1 |
| 8,261,936 | B2 * | 9/2012 | DuMond | G07F 11/44 198/399 |
| 8,281,955 | B2 * | 10/2012 | Farnsworth | B65B 39/001 221/234 |
| 2003/0074868 | A1 * | 4/2003 | Yasuoka | B65B 5/103 53/493 |
| 2004/0104241 | A1 * | 6/2004 | Broussard et al. | 221/289 |
| 2004/0176873 | A1 * | 9/2004 | Kim | G07F 11/44 700/231 |
| 2007/0150092 | A1 * | 6/2007 | Ohmura | G06F 19/3462 700/231 |
| 2008/0255700 | A1 * | 10/2008 | Mitchell | A61J 7/02 700/240 |
| 2009/0039097 | A1 * | 2/2009 | Farnsworth | G07F 11/44 221/1 |
| 2009/0140002 | A1 * | 6/2009 | Farnsworth | B65B 39/001 221/178 |
| 2010/0229506 | A1 * | 9/2010 | Kumano | G07F 17/0092 53/493 |
| 2011/0220689 | A1 * | 9/2011 | Njaastad et al. | 222/639 |
| 2012/0061417 | A1 * | 3/2012 | Farnsworth | B65B 39/001 221/124 |

* cited by examiner

FIG. 11

CASSETTE INFORMATION

| 001 xxxxxxxx | 010 xxxxxxxx | 019 xxxxxxxx | 028 xxxxxxxx | 037 xxxxxxxx | 046 xxxxxxxx |
| --- | --- | --- | --- | --- | --- |
| 002 xxxxxxxx | 011 xxxxxxxx | 020 xxxxxxxx | 029 xxxxxxxx | 038 xxxxxxxx | 047 xxxxxxxx |
| 003 xxxxxxxx | 012 xxxxxxxx | 021 xxxxxxxx | 030 xxxxxxxx | 039 xxxxxxxx | 048 xxxxxxxx |
| 004 xxxxxxxx | 013 xxxxxxxx | 022 xxxxxxxx | 031 xxxxxxxx | 040 xxxxxxxx | 049 xxxxxxxx |
| 005 xxxxxxxx | 014 xxxxxxxx | 023 xxxxxxxx | 032 xxxxxxxx | 041 xxxxxxxx | 050 xxxxxxxx |
| 006 xxxxxxxx | 015 xxxxxxxx | 024 xxxxxxxx | 033 xxxxxxxx | 042 xxxxxxxx | 051 xxxxxxxx |
| 007 xxxxxxxx | 016 xxxxxxxx | 025 xxxxxxxx | 034 xxxxxxxx | 043 xxxxxxxx | 052 xxxxxxxx |
| 008 xxxxxxxx | 017 xxxxxxxx | 026 xxxxxxxx | 035 xxxxxxxx | 044 xxxxxxxx | 053 xxxxxxxx |
| 009 xxxxxxxx | 018 xxxxxxxx | 027 xxxxxxxx | 036 xxxxxxxx | 045 xxxxxxxx | 054 xxxxxxxx |

<< Unit 1 1-64 >>

MENU | Prescription List | Exception List | Drug List | Information | Manual

41

| MANUAL INPUT | | | | |
|---|---|---|---|---|
| No | ID# | Drug Name | Dealer Name | Expiration Date |
| 1 | 015369852 | xxxxxxxxxxxxxxxxx | | |
| 2 | 021574536 | xxxxxxxxxxxxxxxxx | | |
| 3 | 021458745 | xxxxxxxxxxxxxxxxx | | |
| 4 | 036985214 | xxxxxxxxxxxxxxxxx | | |
| 5 | 014785236 | xxxxxxxxxxxxxxxxx | | |
| 6 | 019658236 | xxxxxxxxxxxxxxxxx | | |
| 7 | | | | |
| 8 | 019632584 | xxxxxxxxxxxxxxxxx | | |
| 9 | 014211236 | xxxxxxxxxxxxxxxxx | | |
| 10 | 012365453 | xxxxxxxxxxxxxxxxx | | |

Cassette No  1   Qty.

40DR is the best

OK   CANCEL

TABLET DISPENSER

This application is a Continuation-In-Part of U.S. patent application Ser. No. 13/018,564, filed Feb. 1, 2011, which is a Continuation-In-Part of PCT/JP2009/006195, filed Nov. 18, 2009, which claims the benefit of foreign priority under 35 U.S.C. §119 to Japanese Patent Application Nos. JP2009-193142, filed Aug. 24, 2009, JP2009-048442, filed Mar. 2, 2009, and JP2008-298122 filed Nov. 21, 2008, the entire disclosure of each of which is incorporated herein by reference.

BACKGROUND OF THE INVENTION

The present invention relates to a tablet dispenser and, more particularly, to a semi-automatic tablet dispenser.

There are various types of conventionally known tablet dispensers in the industry, including automatic and semi-automatic dispensers. U.S. Pat. No. 7,412,302 describes a semi-automatic tablet dispenser including a tubular chamber for storing pharmaceutical units and a hopper. Pharmaceutical units are dispensed from the tubular chamber to the hopper, which temporarily stores the units therein, and then dispenses them into a tablet container. However, because the hopper projects directly from the front face of the tubular chamber, this tablet dispenser unavoidably has a large depth, such that the overall structure of the tablet dispenser is complicated and the overall dimensions are inevitably large.

The semi-automated tablet dispenser of U.S. Pat. No. 6,595,384 is configured such that assorted solid medicines are supplied from a solid medicine supplier to a chute and then are dispensed into bottles. However, because assorted solid medicines are all discharged through the same chute, residue from prior solid medicines may adhere to the chute, causing contamination of the chute. Further, as with the tablet dispenser of the U.S. Pat. No. 7,412,302, the final dispensing operation described by U.S. Pat. No. 6,595,384 requires the operator to use two hands, one hand for placing the tablet containers at the dispensing outlet of the chute and another hand for sliding the partition plate 27 upwardly.

U.S. Pat. No. 6,644,504 discloses a fully automatic tablet dispenser, configured to automatically dispense tablets and to supply tablet containers. However, in order to automate the supply of the tablet containers, as well as to dispense tablets, the device structure becomes complicated, resulting in higher manufacturing costs.

BRIEF SUMMARY OF THE INVENTION

Thus, it is an object of the present invention to provide a tablet dispenser that has a simple configuration, is inexpensive and compact, and can facilitate the operation of dispensing tablets into tablet containers.

In order to resolve the aforementioned problems, the present invention is directed to a dispensing chute assembly having a chute configured to receive objects to be dispensed. The chute includes an outlet and a passive dispensing unit attached to the chute outlet. The passive dispensing unit may include a staging portion, wherein objects are captured prior to dispensing. The staging portion further includes a gate member movable between a staging position, in which objects may be captured within the staging portion, and a dispensing position, in which the objects may be fed gravimetrically into a receptacle positioned below the dispensing unit. The dispensing unit further includes a release member, the release member being coupled with the gate member, such that movement of the release member from the staging position to the dispensing position moves the gate member from its staging position to its release position. It should be noted that the gate member does not move perpendicularly relative to the chute, as the gate member moves from the staging position to the dispensing position.

Such a configuration may create an effective and safe touch performance between a tablet container and the release member by a worker who slides down the release member with the tablet container. Thus, the release member moves to the tablet container-side slightly (a downward angle from the worker) which opens the lower opening portion of the chute. This release member movement can avoid the worker to drop tablets during his work in progress.

Further, the gate member moves, from the staging portion to the dispensing position, at least 5 mm in a direction of the receptacle positioned below the dispensing unit. Thus, the gate member can rotate about a pivot attached to the chute in a manner to be able to move upward and open the lower opening portion of the chute.

In one embodiment, the spout may be positioned downstream of the staging portion. Moreover, the spout can be attached to the release member and the spout may include a flexible material that enables the spout to conform to receptacles of different diameters.

In one embodiment, the release member is coupled to the gate member such that gravity biases the release member toward the staging position. Further, the gate member may include a pin, which is received by a slot of the release member.

In order to resolve the aforementioned problems, another embodiment of the present invention is directed to a dispensing chute assembly, including a chute configured to receive objects to be dispensed. The chute having an outlet and a passive dispensing unit attached to the chute outlet. The passive dispensing unit may include staging portion, wherein objects are captured prior to dispensing. The staging portion further includes a gate member movable between a staging position, in which objects may be captured within the staging portion, and a dispensing position, in which the objects may be fed gravimetrically into a receptacle positioned below the dispensing unit. The dispensing unit further includes a release member, the release member being coupled with the gate member, such that movement of the release member from a staging position to a dispensing position moves the gate member from its staging position to its release position. A spout is further positioned downstream of the staging portion which is attached to the release member, the release member moves in concert with the staging portion as the release member moves between the staging and dispensing positions.

With such a configuration, the chute unit may have a simple configuration mainly because the staging portion moves instead of the chute unit. The chute unit becomes larger and more complex configuration is needed if the chute unit moves by itself. That also makes difficult to achieve an inexpensive and simple maintenance unit due to the increasing of replacement parts for the chute unit.

Thus, the release member does not move in concert with the chute as the release member moves between the staging and dispensing position. Moreover, the spout may include a flexible material that enables the spout to conform with receptacles of different diameters. The release member may also be coupled to the gate member such that gravity biases the release member toward the staging position.

In an alternate embodiment, the gate member can move perpendicularly relative to the chute, as the gate member moves from the staging position to the dispensing position.

Further, the gate member may include a pin, which is received by a slot of the release member.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown in the drawings.

FIG. 11 shows the main screen displayed in the liquid crystal monitor of FIG. 1.

DETAILED DESCRIPTION OF THE INVENTION

Figure 1:
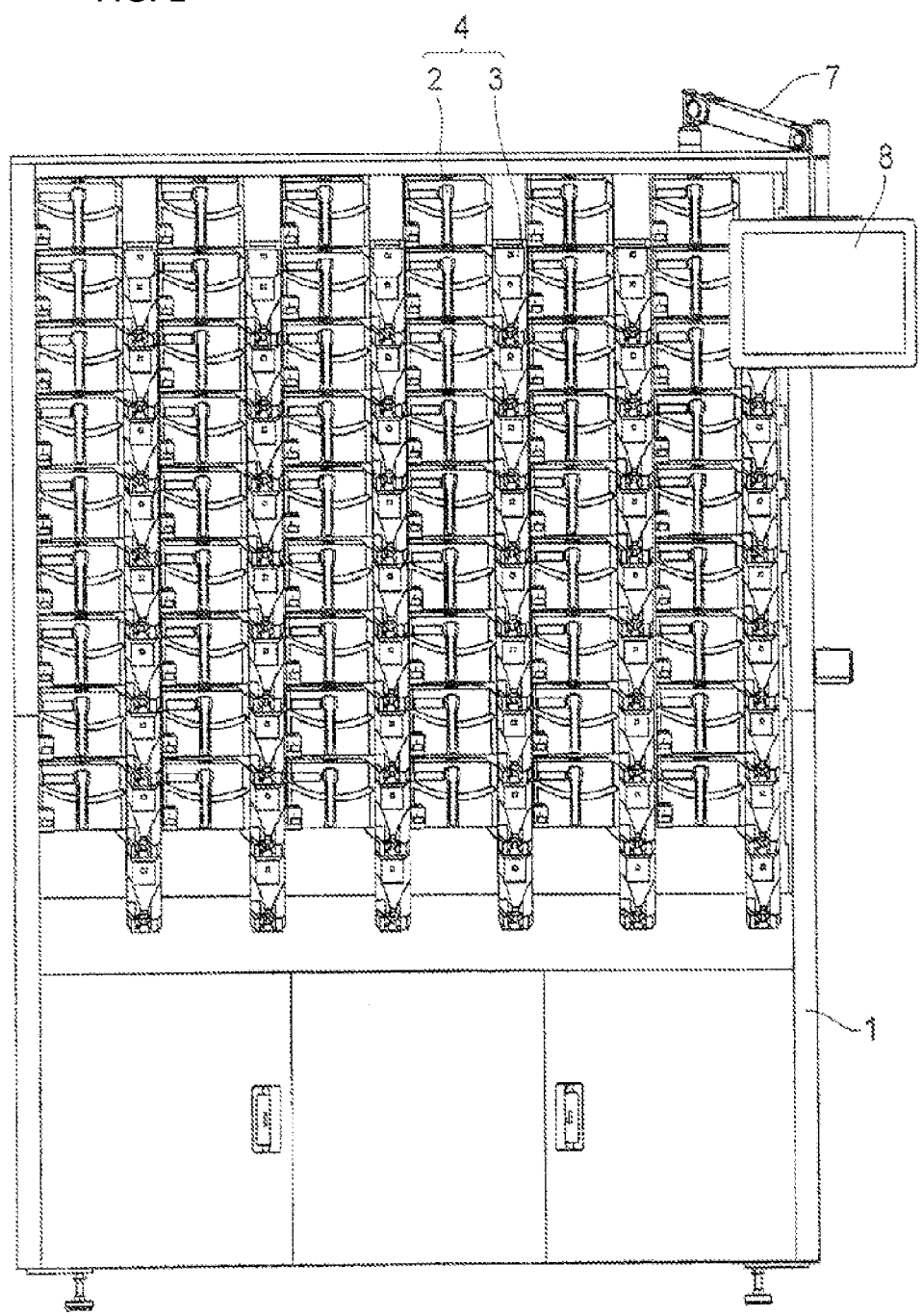
FIG. 1 is a front view of the tablet dispenser according to a first preferred embodiment.

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the collet mechanism and designated parts thereof. Unless specifically set forth herein, the terms "a", "an" and "the" are not limited to one element but instead should be read as meaning "at least one". Terms, such as "above," "below," "side," and "end," will be used as necessary and are being used to facilitate understanding of the invention in reference to the drawings and the meanings of such terms do not place limitations on the technical scope of the present invention. The terminology includes the words noted above, derivatives thereof and words of similar import.

Figure 2:
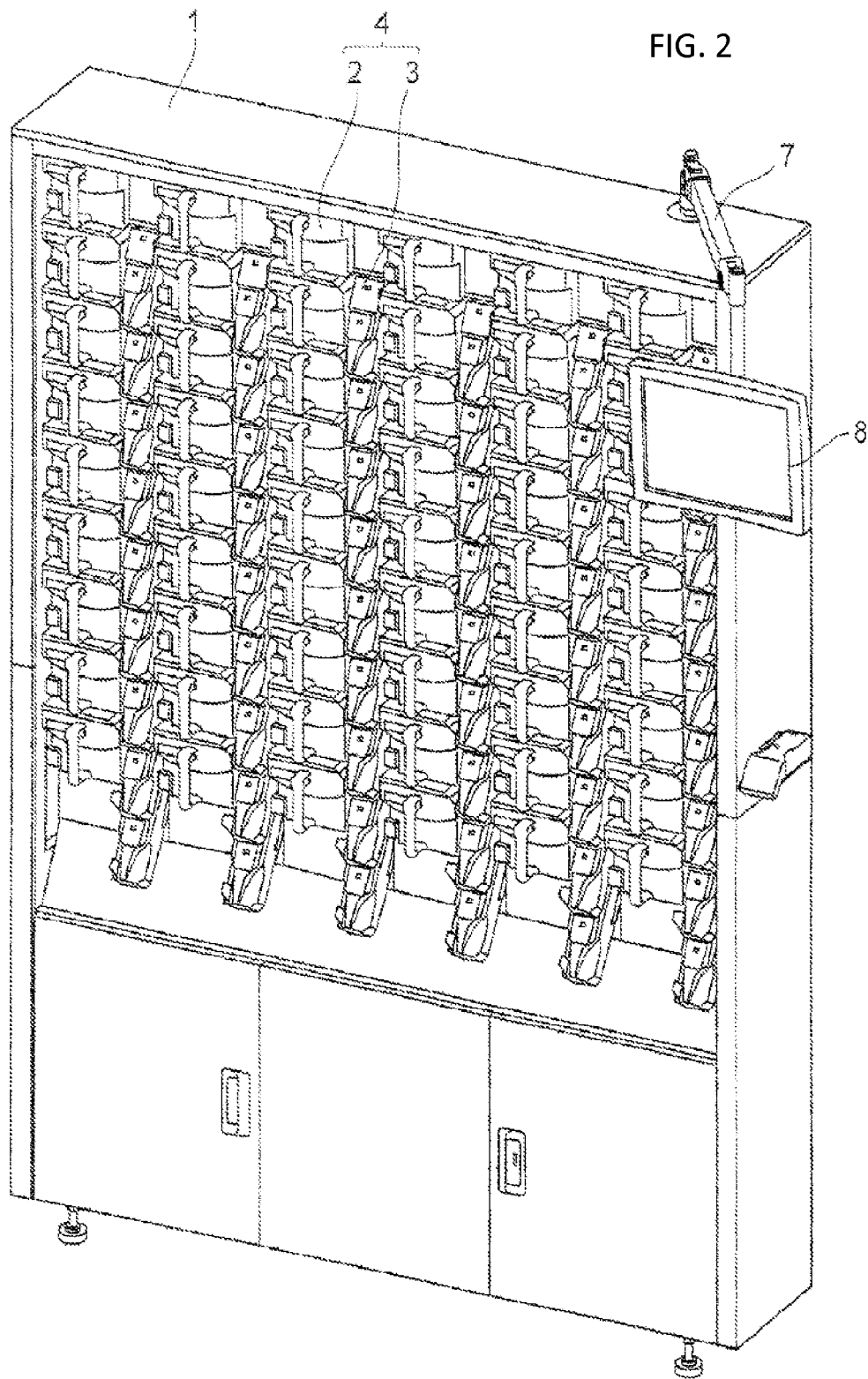
FIG. 2 is a perspective view of the tablet dispenser according to the first preferred embodiment.

FIGS. 1 and 2 show a tablet dispenser according to a first preferred embodiment. The tablet dispenser comprises a device body 1. A plurality of dispensing units 4 are disposed on one face of the device body 1 in vertical and horizontal rows. Each dispensing unit 4 comprises a tablet cassette 2 and a chute 3, wherein each chute 3 is disposed adjacent to a corresponding tablet cassette 2 and is in communication with the corresponding tablet cassette 2. Each tablet cassette 2 is capable of accommodating a plurality of types of tablets and dispenses the tablets contained therein in a lateral direction. A control unit 5 controls such processes as the dispensing of the tablets from the tablet cassette 2. The tablets discharged from the tablet cassette 2 accumulate and are retained in the corresponding chute 3. The chute 3 dispenses the tablets in a downward direction, such that they are manually collected in a tablet container 6 (See FIG. 6).

The tablet container 6 used here is made of synthetic resin and comprises a closed bottom, a tubular body, and a flange 6a formed at the outer periphery near the upper opening edge of the tablet container 6. While the tablet container 6 depicted in FIG. 6 has a circular cross section, it will be understood by those skilled in the art that the tablet container 6 may have any appropriate shapes, such as a rectangular, hexagonal or other polygonal cross section. Further, it will be understood by those skilled in the art that the tablet container 6 may be made of any appropriate material and may be any appropriate size, depending on the size and number of tablets to be accommodated.

The device body 1 has a roughly rectangular shape and the dispensing units 4 are detachably arranged in vertical and horizontal rows. The tablet cassettes 2 and chutes 3 are arranged vertically, with shifted horizontal positions. Thus, the tablet cassettes 2 are disposed with virtually no gaps there between in the vertical direction. The chutes 3 are configured so as to project obliquely forward and downwardly away from the one face of the device body 1. The chutes 3 are positioned such that the lower portion of one chute 3 overlaps with the upper portion of the chute 3 that is positioned immediately below it. With such an overall configuration, when tablets are dispensed from a top chute 3, the lower chute 3, positioned immediately below the top chute 3, serves as a guide for placement of the tablet container 6 into which tablets are dispensed from the top chute 3.

Further, the device body 1 is provided with an arm 7 on the top surface thereof and the leading end of the arm 7 is provided with a liquid crystal monitor 8. The liquid crystal monitor 8 comprises a touch panel and display screen, which displays a main screen at start up, as shown in FIG. 11. The main screen displays cassette information, including cassette number, medicine name, indicator and the like, for each tablet cassette 2 provided in the device body 1. An indicator can be configured, for example, from a display unit (not shown) that emits light in three different colors. In cases where the same type of tablet is included in a plurality of prescription data, the indicator lights up to indicate that there will be a subsequent dispensing process. More specifically, the display can be configured to light up in two places when there are two waiting prescriptions.

Figure 3:
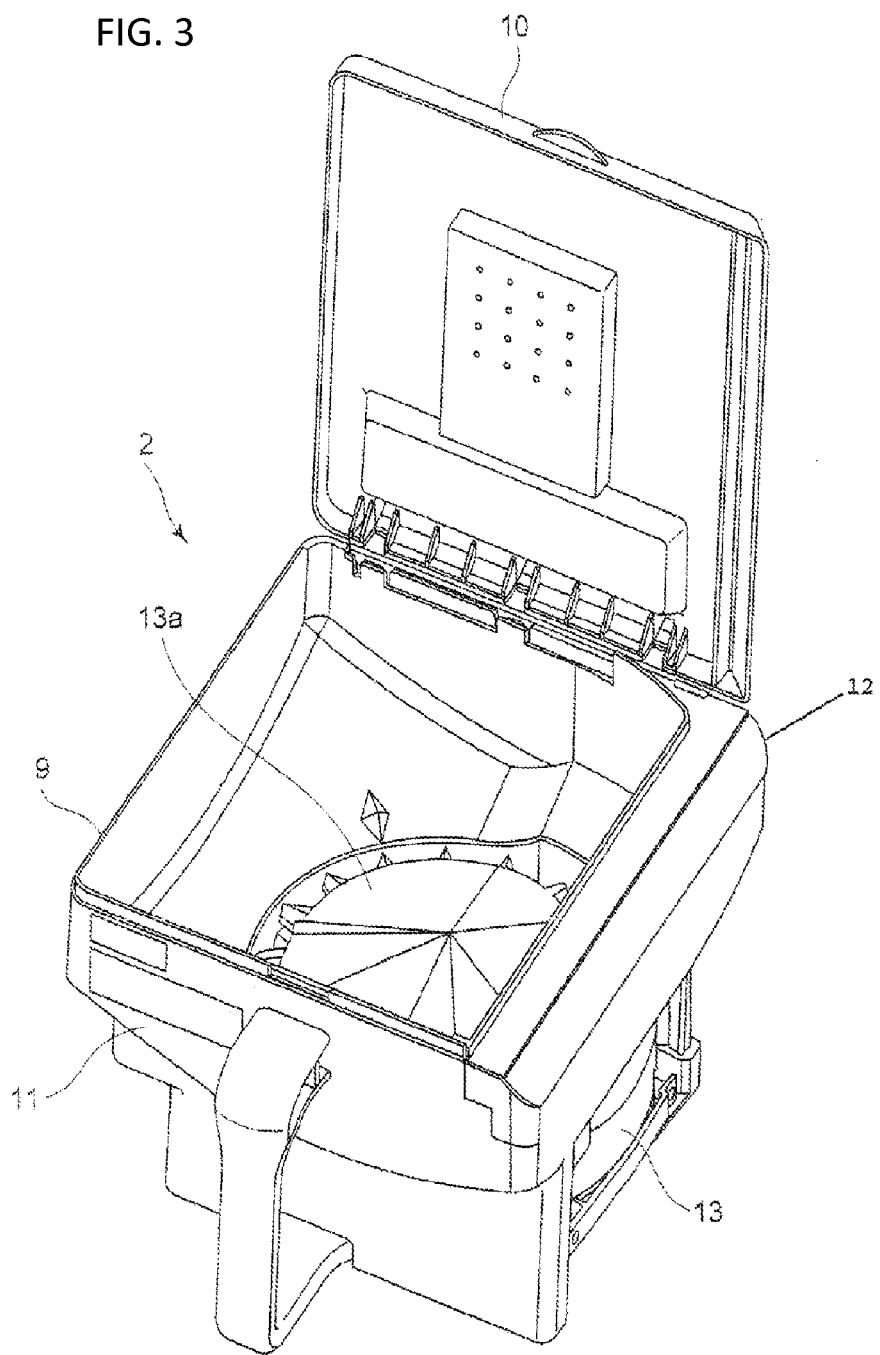
FIG. 3 is a perspective view of the tablet cassette of FIG. 1.
Figure 4:
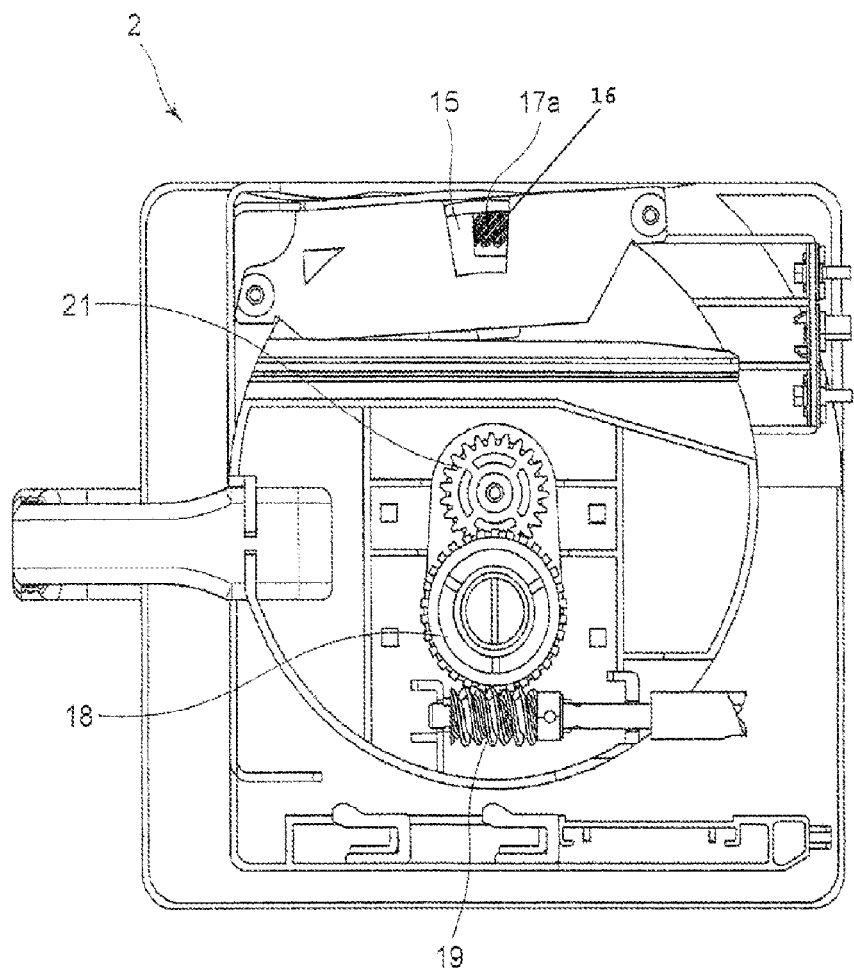
FIG. 4 is a bottom view of the tablet cassette of FIG. 1.
Figure 5:
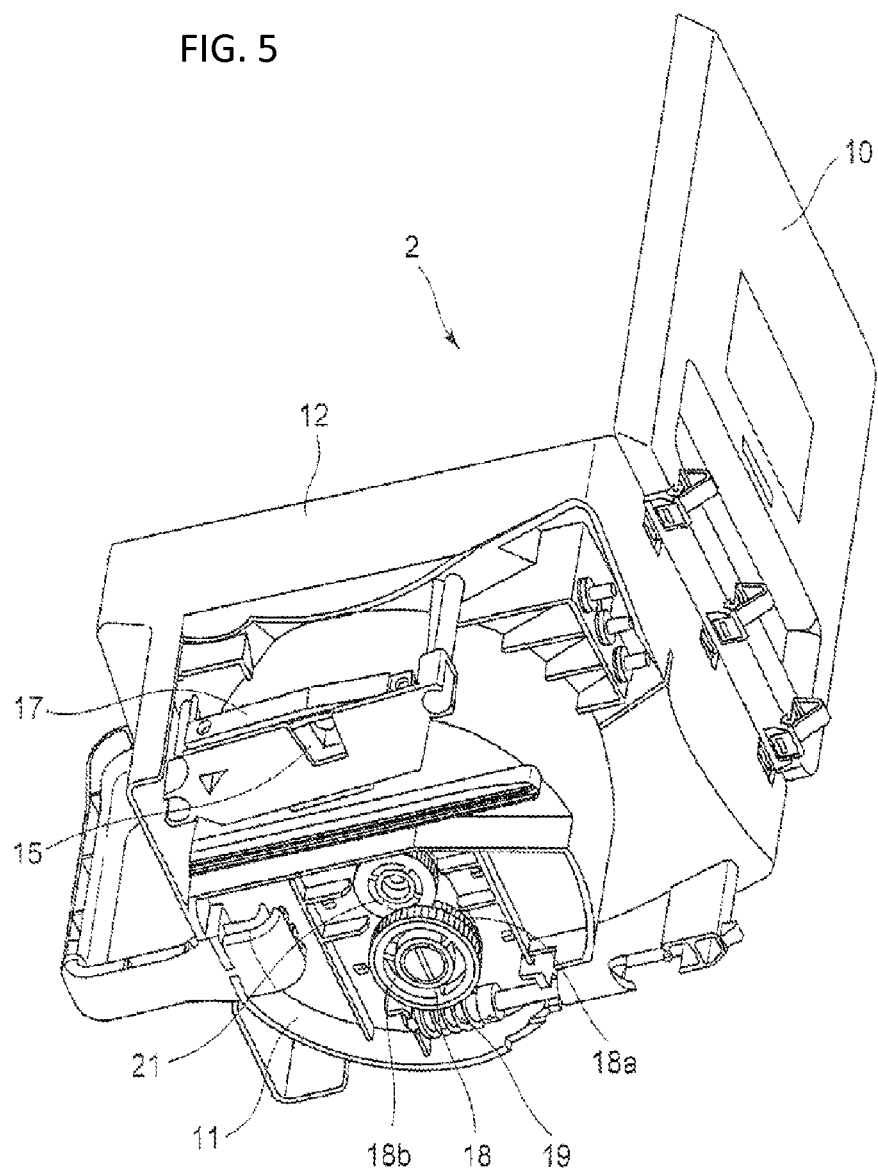
FIG. 5 is a perspective view seen from the bottom side of the tablet cassette of FIG. 1.

As shown in FIGS. 3 through 5, the tablet cassette 2 comprises a cassette body 9 having an open-close lid 10. Each tablet cassette accommodates a large number of a certain type of tablet. If certain tablets are dispensed more often than others, those medicines may be accommodated in more than one tablet cassette 2. Each tablet cassette 2 can be attached to and detached from the support table of the device body 1. However, when a tablet cassette 2 is attached to the device body 1, it cannot be freely removed therefrom due to a lock mechanism (not shown).

Each cassette body 9 comprises a tubular rotor accommodation part 11 and a tablet accommodation part 12 positioned above the rotor accommodation part 11 and having a generally rectangular shape. The tablet accommodation part 12 has a space formed by the lateral walls and the upper surface (conical surface 13a) of a rotor 13, and is capable of accommodating tablets. The rotor accommodation part 11 has a tablet outlet 15 (see FIG. 5) and a slit 16 formed on a lateral portion thereof. A separating member 17 is fixed in the vicinity of the slit 16 and a brush part 17a of the separating member 17 projects through the slit 16 into the rotor accommodation part 11.

Further, the rotor accommodation part 11 has an aperture (not shown) in the center of the bottom surface and an intermediate gear 18 rotatably attached around the aperture. The intermediate gear 18 is structured such that a first gear 18a and second gear 18b are integrally provided in a row in the axial direction. A worm gear 19 is attached to the bottom surface of the tubular rotor accommodation part 11 and engages with the second gear 18b of the intermediate gear 18. The drive force from a motor 20 is transmitted via the worm gear 19 to the intermediate gear 18 so as to rotate the rotor 13.

The rotor 13 has a cylindrical shape and includes a conical surface 13a, the upper surface of which projects toward the center of the rotor 13. An axially extending guide groove (not shown), formed on the outer periphery surface of the rotor 13, accommodates tablets in a vertical and orderly manner. The tablets in the guide groove are vertically separated by the brush part 17a of the separating member 17, such that only the one tablet below the brush part 17a drops through the tablet outlet 15. A rotary shaft is integral with the rotor 13 and provided at a center portion of the bottom surface of the rotor 13. Specifically, the rotary shaft passes through the aperture formed in the bottom surface of the rotor accommodation part 11. A driven gear 21 is fixed to the projecting portion of the rotary shaft. The driven gear 21 engages with the first gear 18a of the intermediate gear 18, such that when the worm gear 19 rotates, the driven gear 21 and rotor 13 rotate via the intermediate gear 18.

Figure 6:
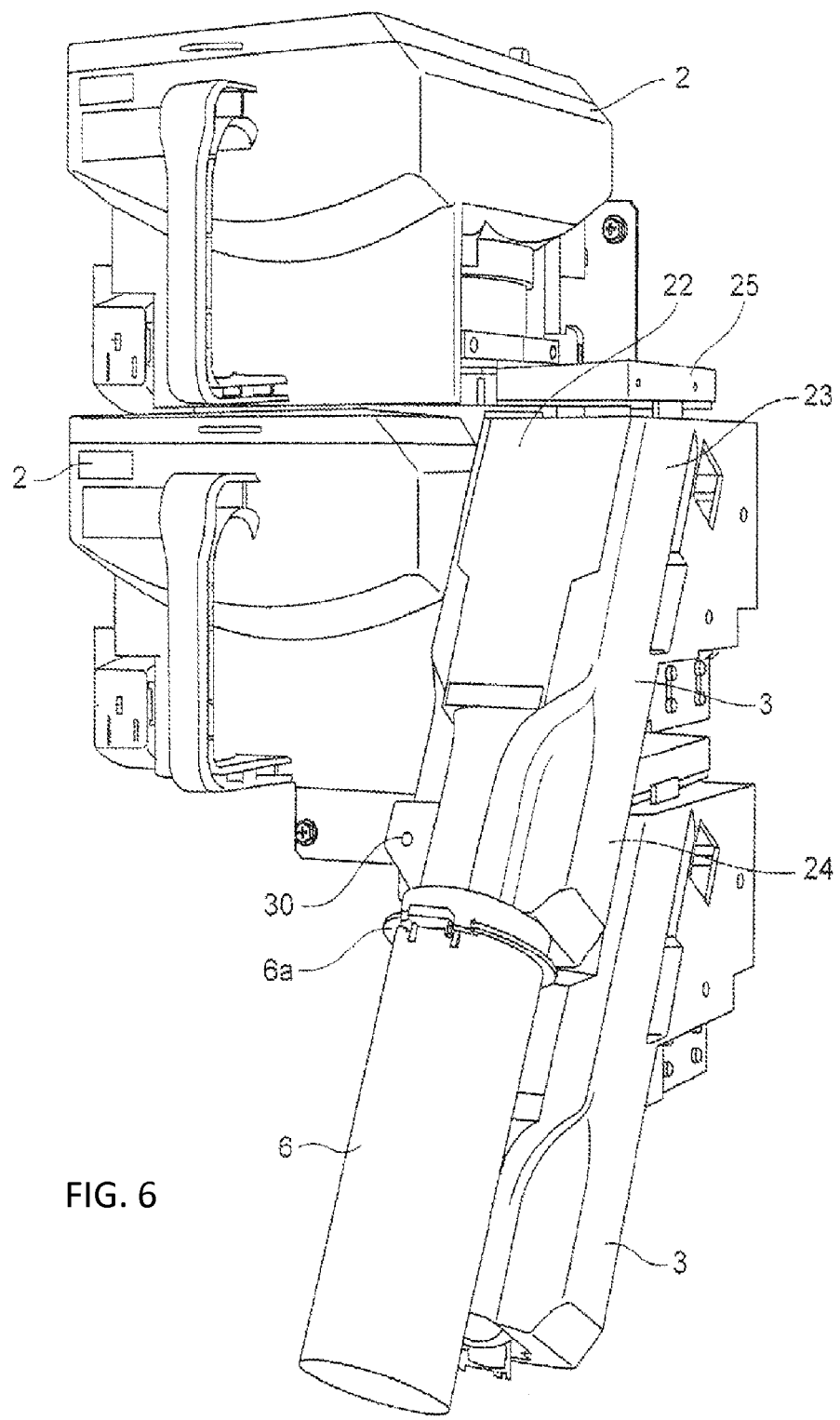
FIG. 6 is a perspective view of two sets of the tablet cassette and chute of FIG. 1.
Figure 7:
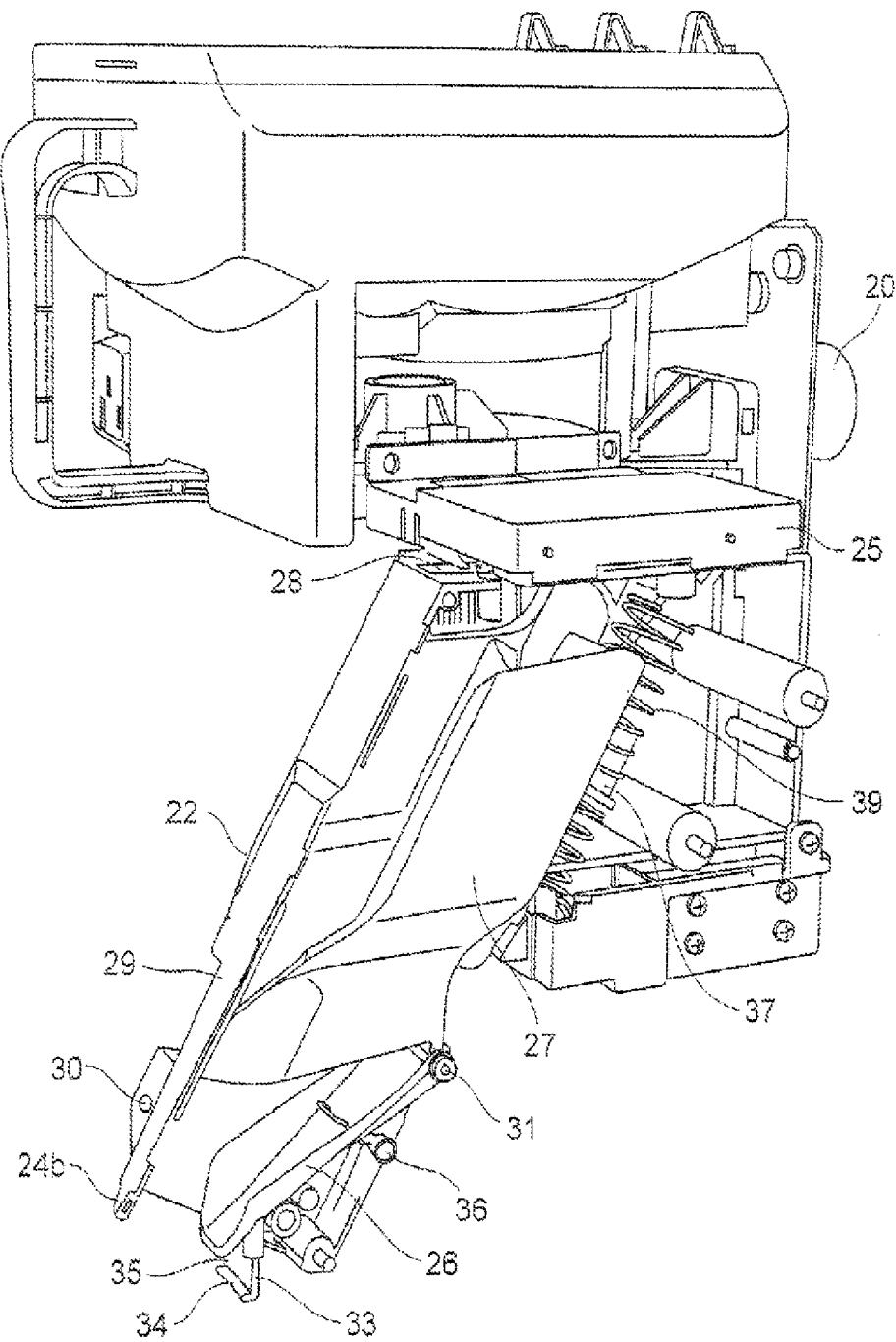
FIG. 7 is a perspective view showing the chute shown of FIG. 1 with the second cassette removed.
Figure 9:
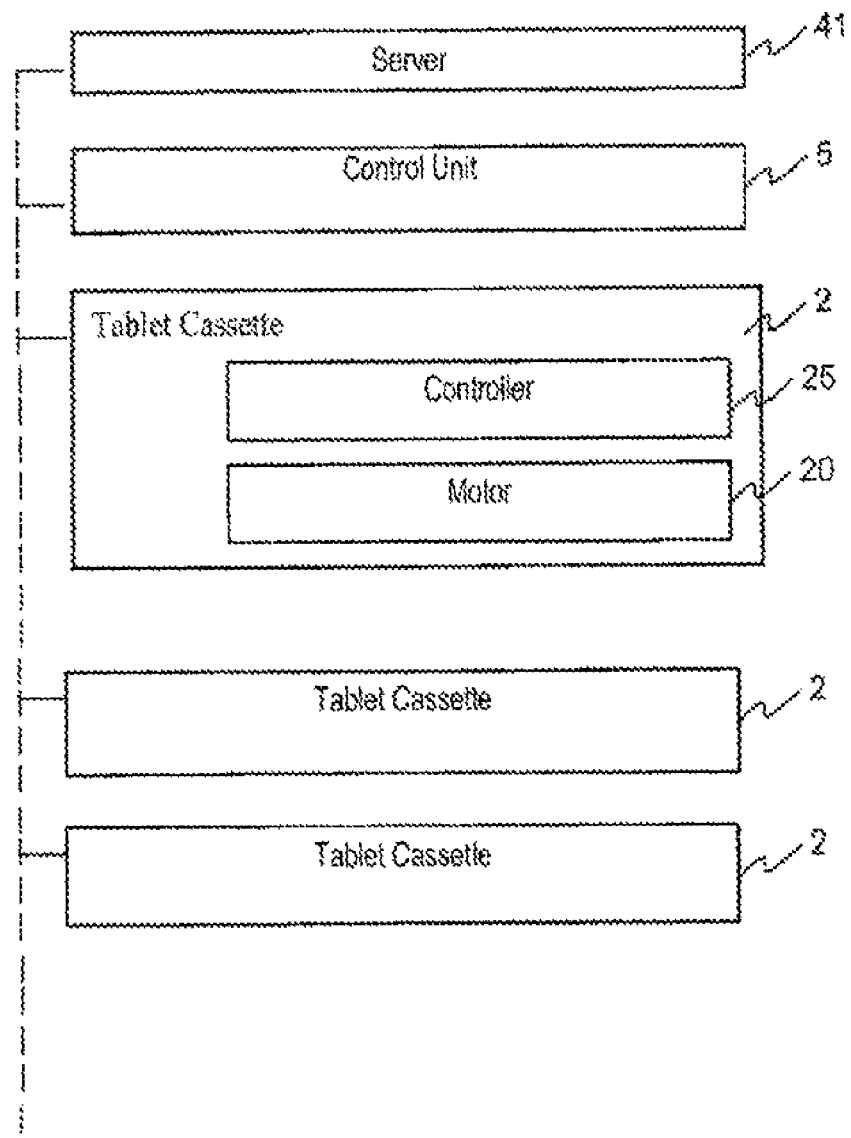
FIG. 9 is a block diagram of the tablet dispenser according to the first preferred embodiment.

As shown in FIGS. 6 and 7, each chute 3 comprises a guide path 24 on its front surface. The guide path 24 is divided into left-hand and right-hand components, such that the guide path 24 is formed by a first case 22 and a second case 23. The upper surface of each chute 3 is provided with a controller 25 comprising assorted electronic parts mounted on a printed wiring board. The controller 25 detects the drive state of the motor 20. Specifically, the controller 25 detects the number of dispensed tablets based on the detection signal generated by a tablet detection sensor (not shown) and then outputs the results to the a control unit 5 (FIG. 9). Then, in response to the control signal from the control unit 5, the motor 20 is driven and controlled so as to rotate the rotor 13.

In the present invention, a tablet is detected in accordance with the time at which the tablet goes through the tablet detection sensor, (not shown) in order to distinguish a tablet discharged from the tablet cassette 2 from a chip of a tablet or powder dust.

Specifically, five tablet detection sensors are provided. A total value is obtained by integrating the difference between an A/D converted value and a long-period average converted value of each sensor and comparing the integrated value with a tablet pass timing (a threshold value), which is determined in accordance with the size or figure of a tablet to be accommodated in each cassette preliminarily. When the result is out of the determined timing, for example, the total value which is obtained by integrating is lower than the determined timing, and the detected thing is judged as a thing out of a tablet including a fragment, etc. and is not counted, i.e. omitted.

More specifically, a peak value of an A/D converted value when a tablet (or a fragment, etc.) goes through each sensor with respect to a predetermined period is memorized. When the peak value becomes the value which can be considered as not a tablet, it is compared with the predetermined pass timing, for example, four step threshold values determined by the kind of medicine. In the case that the total of the peak value exceeds the pass timing, it is judged that an appropriate tablet passes through the sensor. In the case that the total does not exceed the pass timing, it is judged that a fragment, etc. passes through the sensor and is not counted.

In addition, when the detection values detected by some of the sensors simultaneously change, it is possible to set that the values are considered as a noise.

Figure 8:
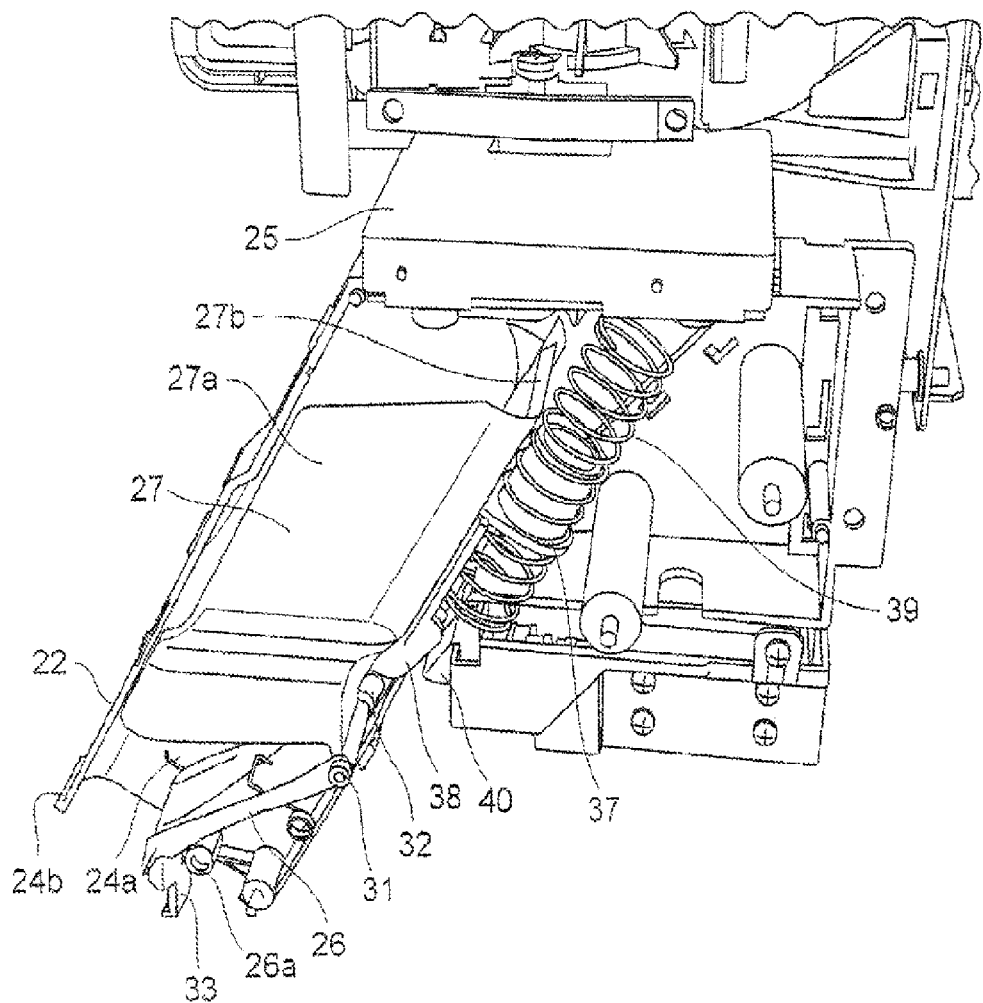
FIG. 8 is a perspective view showing the chute of FIG. 7 seen from a different angle.

Referring to FIGS. 7 and 8, the guide path 24 projects obliquely downward in a forward direction. A gate plate 26 and a slide plate 27 are provided therein. An opening is formed in the upper surface of the guide path 24 at the side of the tablet cassette 2 and a guide part 28 is attached thereto in order to guide the tablets dispensed from the tablet cassette 2 into the tablet container 6. The guide part 28 comprises an inclined surface that extends obliquely toward the tablet outlet 15 of the tablet cassette 2 and has a plurality of projecting stripes provided along the tablet discharge direction. The guide path 24 further has a portion 29 of restricted flow, formed at an intermediate point of the guide path 24. The portion 29 of restricted flow of the guide path 24 has a cross-sectional area that gradually reduces toward the direction in which tablets are dispensed from the chute 3. More specifically, the upper portion of the guide path 24 has a larger cross-sectional area than the lower portion and is capable of accumulating a large amount of tablets. The cross-sectional area gradually reduces from the upper portion toward the lower portion, such that the lower portion has an opening area of a size suitable for dispensing tablets into tablet containers 6. Thus, the lower portion of the guide path 24 comprises an opening through which tablets may be dispensed.

At least the front face of the guide path 24 is made of a translucent material, enabling an operator to observe generally how many tablets are accommodated in the chute 3, and is marked with lines indicating the number of tablets accommodated in the chute 3. An operator can use these lines to determine, at a glance, how many tablets supplied from the tablet feeder have been accumulated in the chute 3. Thus, an operator can determine whether the tablet container 6 into which the tablets are to be dispensed is of a sufficient size. The front face of the guide path 24 further has a display 30 provided with a red and a blue light emitting diode (LED), which turn on and off to indicate that tablets will be dispensed from the tablet cassette 2 or some other event.

Each guide path 24 further has a gate member, comprising a gate plate 26 and a slide plate 27, attached thereto. The gate plate 26 is capable of alternately covering and exposing the opening of the chute 3. The gate plate 26 is rotatable around a pivot 31 between an open position and a closed position. The pivot 31 is slidable along a guide groove 32 formed in a lateral wall of the guide path 24. The gate plate 26 has a leading end formed in an arc shape. A tab or pressure receiver 33 is formed on the exterior surface of the gate plate 26 toward the leading end and extends perpendicularly away from the exterior surface of the gate plate 26. When the gate plate 26 is in the open position, the opening of the chute 3 is exposed and tablets may be dispensed there through.

When the gate plate 26 is in the closed position, the pressure receiver 33 projects out from the opening of the guide path 24. An abutment or guide pin 26a is provided near the pressure receiver 33 and is configured to move in a direction parallel to the lower end opening along a guide groove 24a formed in the guide path 24. Thus, when the gate plate 26 is pivoted and rotated from the closed position to the opened position, the dimensions of the pressure receiver 33 do not change and displacement of the container 6 is prevented. A locking projection 34, bent forward at a right angle, is provided at the leading end of the pressure receiver 33. Further, the front surface of the pressure receiver 33 comprises a slip prevention part 35 made of rubber or a like substance. When a tablet container 6 is placed into contact with and used to push against the front face of the pressure receiver 33, the locking projection 34 abuts the outer periphery of the open end of the tablet container 6 and the slip prevention part 35 abuts the outer periphery edge of the flange formed at the open end of the tablet container 6, preventing any displacement of the tablet container 6 with respect to the pressure receiver 33.

When the pressure receiver 33 is pushed toward the rear surface side of the guide path 24, the gate plate 26 rotates around the pivot 31 and exposes the lower end opening of the guide path 24. However, the gate plate 26 is spring-loaded toward the closed position by a closing spring 36 provided on the rear surface side thereof. Thus, when the gate plate 26 rotates toward the closed position and the guide pin 26a slides on the guide groove 24a, the closing spring 36 alleviates the load received by the guide pin 26a using the downward impelling force from a coil spring 39, received by the gate plate 26, causing the gate plate 26 to close smoothly.

The slide plate 27 is formed in a roughly L-shape and comprises portions of the inner surface of the guide path 24. The slide plate 27 moves in conjunction with the gate plate 26. Specifically, the slide plate 27 is comprised of a lateral side 27a, positioned opposite the tablet cassette 2, and a rear side 27b, positioned over roughly half of the rear face of the tablet cassette 2. The lower side of the slide plate 27 curves in correspondence with the guide path 24, such that the slide plate 27 guides tablets to be dispensed toward the gate plate 26. The lower end of the slide plate 27 is connected to the pivot 31 of the gate plate 26, such that the slide plate 27 moves up and down the guide path 24 together with the pivot 31 moving along the guide groove 32. This up and down movement of the slide plate 27 prevents clogging or jamming of the tablets accumulated in the guide path 24.

The slide plate is spring-loaded toward the closed position when the slide plate is in the lower position and the opening of the guide path 24 is covered. A spring receiver 37 and an engagement receiver 38 are provided on the rear face of the rear side of the slide plate 27. The spring receiver 37 holds the coil spring 39, which is pressed against the top surface of the first case 22 and the second case 23, thereby impelling the slide plate 27 in a downward direction. Thus, when the applied force is released from the pressure receiver 33 of the gate plate 26, the slide plate 27 is automatically restored to its original lower position. Further, the engagement receiver 38 engages with and separates from an engagement part 40 provided at the leading end of a rod that advances and recedes in response to the excitation/demagnetization of a solenoid. When the slide plate 27 is positioned at the lower or closed position, the engagement part 40 can engage with the engagement receiver 38, and its positioning is set there. Accordingly, when both the gate plate 26 and the slide plate 27, which move in conjunction with each other, are in the closed position, tablets are prevented from discharging from the chute unintentionally.

Each guide path 24 further comprises a removable cover. A manually or electrically actuated interlock (not shown) is provided on each chute 3 and has a first position and a second position. In the first position, the interlock secures the removable cover of the guide path 24 to each chute 3. In the second position, the interlock retains the gate plate 26 and slide plate 27 to expose the opening of each chute 3. In the second position, the cover of the guide path 24 may be removed, such that a user may clean the interior of the chute 3 of any accumulated pharmaceutical powder without the risk of tablets being dispensed during the cleaning operation.

The control unit 5 (FIG. 9) uses prescription data that is input from a server 49 or the like as the basis for executing a series of tablet dispensing processes, such as driving and controlling the relevant tablet cassette 2 to cause tablets to be dispensed into the chute 3, as described below.

Figure 10:
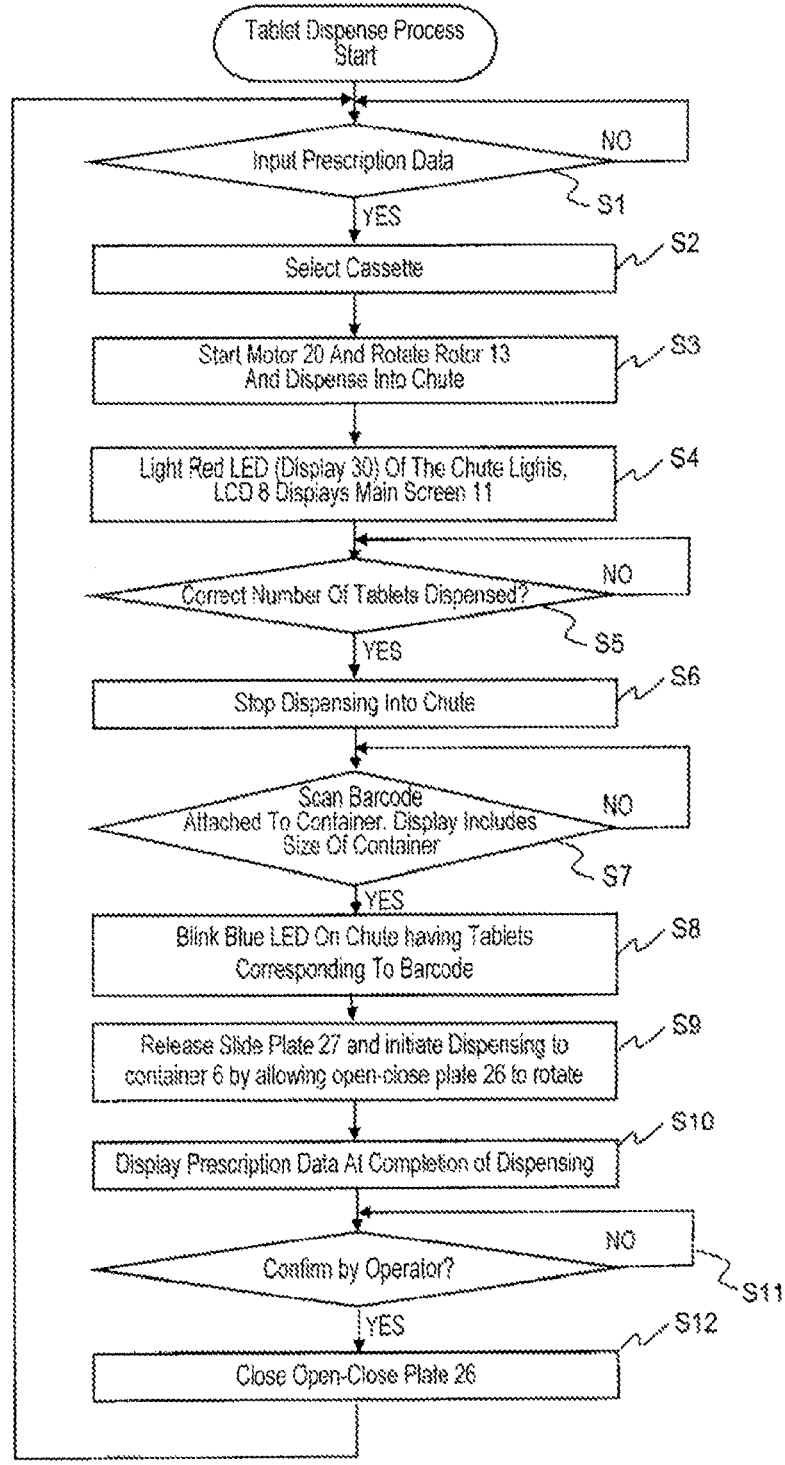
FIG. 10 is a flowchart describing the dispensing process according to the first preferred embodiment.
Figures 13, 14:
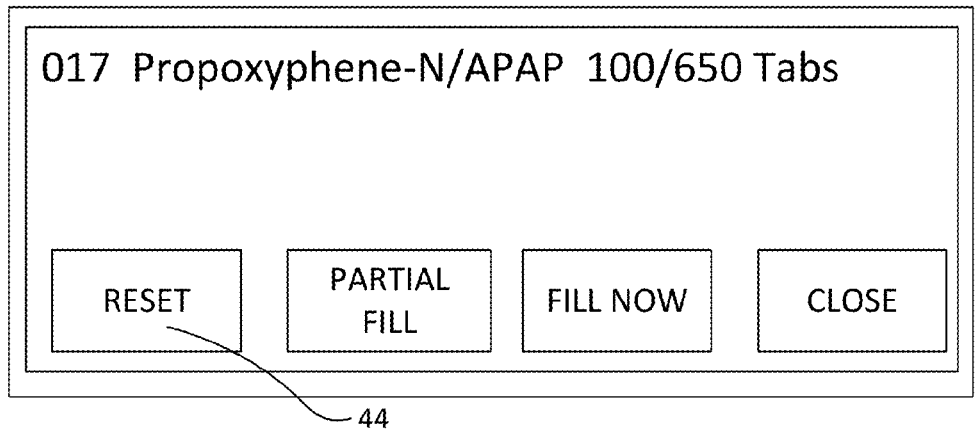
FIG. 13 shows the dispensing information screen displayed in response to touch operations of the tablet cassette area on the main screen.
FIG. 14 shows the manual input screen displayed on the liquid crystal monitor of FIG. 1.

Next, the operation of a tablet dispenser having the above configuration will be explained according to the flowchart shown in FIG. 10. When prescription data is input from a server or the like (not shown) (step Si), the tablet cassette 2 holding the desired prescriptive is identified based on such (step S2). According to the process represented by FIG. 10, the prescription data is automatically input. However, the prescription data may alternatively be manually input by an operator using a manual input screen as shown in FIG. 14. Then, the motor 20 of the identified tablet cassette 2 is driven and the rotor 13 is rotated, initiating a tablet dispensing operation (step S3). At this time, the red LED of display 30 of the chute 3, corresponding to the tablet cassette storing the desired tablets, lights up (step S4) to indicate to the operator that the desired type and number of tablets are being dispensed into the chute 3. Further, the liquid crystal monitor 8 displays the main screen as shown in FIG. 11. The main screen 41 is composed of a plurality of cassette displays 41a which display the layout of the cassettes 2 and are placed as matrix-like, and include several kinds of buttons positioned at the lower side of them. The display form of the cassette displays 41a (background color, color of display character, etc.) is changed in response to the state of the tablet cassette 2. Herein, a frame portion of background is displayed as blue color, the cassette number is displayed therein and the medicine name is shown in the middle of it. When the number of tablets dispensed into the chute 3 is equivalent to the number of tablets specified in the input prescription data (step S5), the motor 20 is switched off and the tablet dispensing operation ceases (step S6). The red LED remains lit at this point. Moreover, in the event that a missing part of medicine has occurred during the dispensing operation, a frame portion of the cassette column 41a is changed to a red color display. In the event that the prescription is canceled, the color of the medicine name is changed to a red color while maintaining the frame portion as a blue color. In addition, the display form is changed such that a user can discriminate in the case of prescription error, prescription cancel, unregistered medicine, unattached cassette and the like. Thus, a user can recognize the state of each cassette 2 at a glance and the workability can be advanced.

Figure 26:
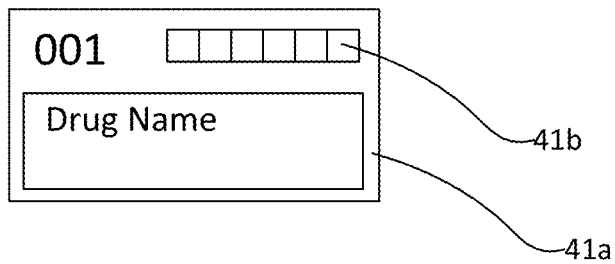
FIG. 26 shows a cassette column displayed in the main screen of FIG. 11.

Further, in the event that a next prescription date including tablets which should be dispensed from the chute 3 is inputted (waiting prescription) before the tablets dispensed from the chute 3 are collected from the tablet cassette 2 into the tablet container 6 based on the prescription data, the display of the cassette display 41a (FIG. 26) is changed. That is, an indicator 41b (here, five square blanks arranged in a lateral direction) is displayed. While a next prescription data is temporarily memorized in the memory portion of the control unit 5, the indicator 41b displayed on the cassette column 41a of the main screen 41 (see FIG. 11) in the liquid crystal monitor 8 is blinked. Herein, the first blank of the five blanks is blinked (for example, as green), so as to inform that the first prescription is in the waiting state. Furthermore, if there is a next prescription, the second blank may be blinked and it becomes possible to deal with waiting data of maximum five descriptions (in this case, a description data is temporally memorized in the memory portion of the control unit 9 in series.)

Figure 27:
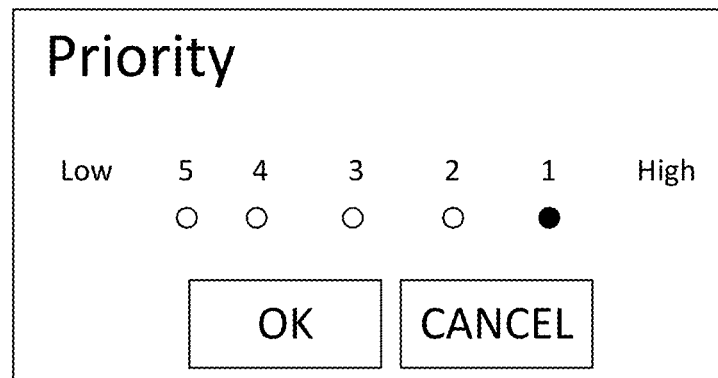
FIG. 27 shows a priority determined column displayed on the liquid crystal monitor of FIG. 1.
Figure 28:
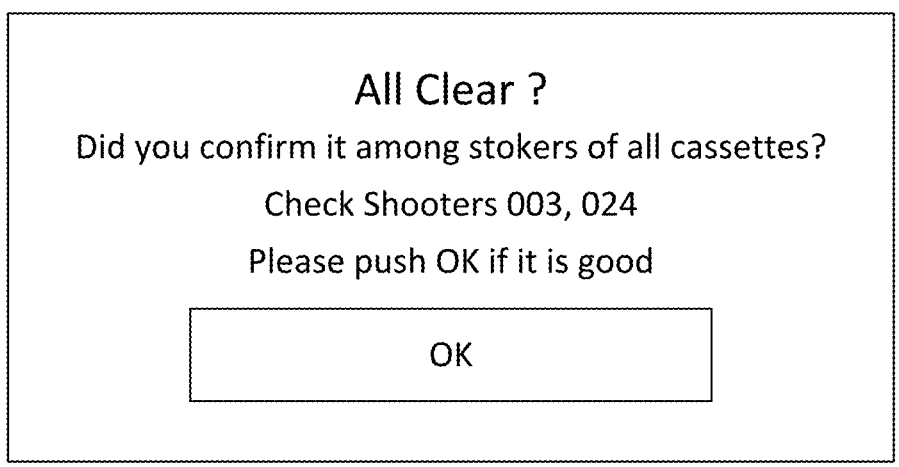
FIG. 28 is a initialization completed screen displayed on the liquid crystal monitor of FIG. 1 and shows the state which a tablet cassette is remained in the chute.

In the case that tablets included in a plenty of waiting prescriptions are accommodated in one chute 3, it is possible to dispense the tablets in accordance with the predetermined priority order. For example, it is possible to display the priority determination column shown in FIG. 27 and set the priority rank of a prescription data (here, five steps). Thus, in the case that there are a plenty of waiting prescriptions to a chute 3, it is possible to dispense tablets which should be dispensed first according to the priority order despite its waiting order.

In addition, the indicator can be utilized during a division prescription as described below.

Figure 12:
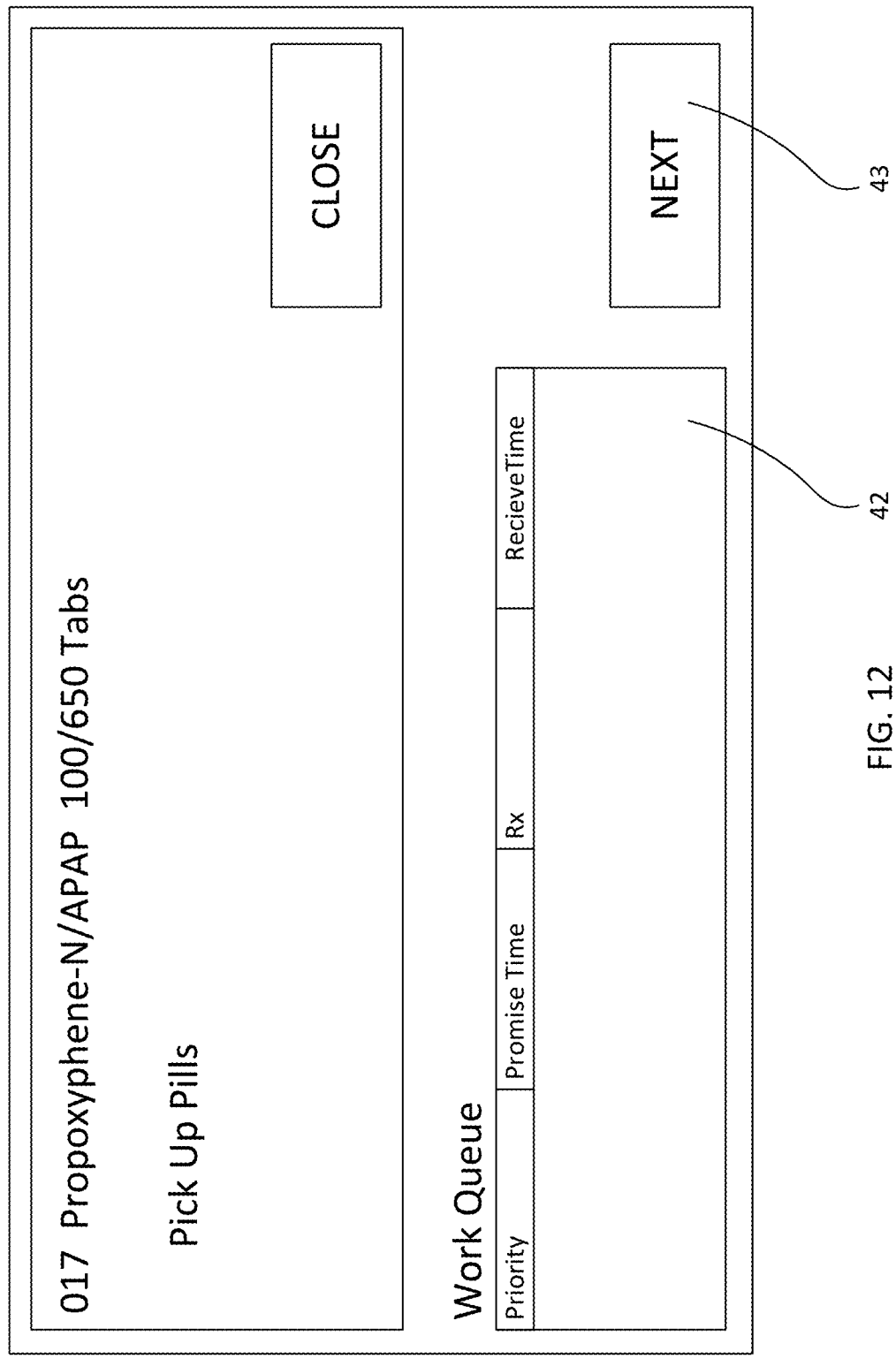
FIG. 12 shows an information screen displayed as a popup on the main screen of FIG. 11.

A barcode is developed in accordance with the prescription data and disposed on the tablet container 6 into which the desired tablets are to be dispensed. After the desired tablets have been dispensed into the chute 3, the barcode is scanned by a barcode scanner (step S7) and the blue LED of display 30 of the chute 3 in which the desired tablets are accumulated begins to blink (step S8). Thus, the operator can tell at a glance from which chute 3 the tablets will be dispensed. Further, at this point, a solenoid is driven, such that engagement part 40 and engagement receiver 38 of the slide plate 27 are released from engagement (step S9). Thus, movement of the gate plate 26 becomes possible. The liquid crystal monitor 8 displays a pop-up information screen as shown in FIG. 12. Preferably, the information screen displays the suitable size of the tablet container 6 to be used, as calculated based on the number of the tablets to be dispensed from the tablet cassette 2 to the chute 3. For example, the information screen may state "40DR is the best!" In another possible configuration, when the prescription data of a plurality of succeeding prescriptions is input, such that there are prescriptions waiting to be dispensed from tablet cassettes, the waiting prescription data is displayed in a "Work Queue" column 43, such that an operator can switch the order of the operation by a "Next" button 42.

Next, the operation of dispensing the tablets from the chute 3 to the tablet container 6 may be initiated. Because the guide path 24 has a translucent front surface and is provided with lines indicating volume, the operator can determine at a glance whether the tablet container 6 is suitable for all of the tablets in the chute 3 that are to be dispensed. Accordingly, an operator need not worry about using the wrong size tablet container 6.

During the tablet dispensing operation, an operator positions the tablet container 6 against the pressure receiver 33 of the chute 3 with the blinking blue LED (display unit 30), such that the open end of the tablet container 6 abuts the pressure receiver 33. In this position, the locking projection 34 abuts the outer periphery surface of the tablet container 6 and the slip prevention part 35 abuts the flange. Thus, even when the tablet container 6 is pushed against the pressure receiver 33, the tablet container 6 is not displaced. Further, as the pressure receiver 33 is pushed against by the tablet container 6, the gate plate 26 rotates around the pivot 31, such that the lower end opening of the guide path 24 gradually becomes exposed. The guide pin 26a also moves in the guide groove 24a in conjunction with the rotation of the gate plate 26. Thus, without changing the direction or orientation of the force applied upon the pressure receiver 33, the position of the open end of the tablet container 6 moves in a direction parallel to the open end of the guide path 24. As such, the dispensed tablets are smoothly accommodated in the tablet container 6 without falling out or spilling.

Further, the pivot 31 moves along the guide groove 32, and the slide plate 27 moves in an upward direction in conjunction with movement of the gate plate 26. Thus, any tablets accumulated in the chute 3 or guide patch 24 and jammed or stuck toward the upper part thereof are forcibly jarred by the slide plate 27, such that the tablets become free to move through the chute 3 to be dispensed into the tablet container 6 from the guide path 24. When the container locking part 24b provided at the lower end of the guide path 24 comes into contact with the inner surface of the open end of the tablet container 6, the rotation of the gate plate 26 is inhibited, and a degree of exposure of the area defining the opening of the tablet container 6 is obtained. In other words, a degree of the exposure of the opening of the guide path 24 or chute 3 corresponds to the size of the open end of the tablet container 6, preventing the problem of tablets falling out and also causing tablets to be dispensed into the tablet container 6 one at a time.

When the dispensing of the tablets from the chute 3 to the tablet container 6 is thus completed, the liquid crystal monitor 8 displays the prescription data of the dispensed tablets (step S10). For example, the prescription data that is displayed may include patient data or the like. The operator then confirms that the information displayed is correct and performs a confirmation operation, by touch-operating, for example, a "confirmation" button displayed in the liquid crystal monitor 8. Once the confirmation operation is executed (step S11), the solenoid is driven, and the gate plate 26 is locked in the closed position (step S12). By such a procedure, the series of tablet dispensing processes is completed.

a. Interruption

In the event an interruption process must be performed, whereby prior to the dispensing of the tablets dispensed into and accumulated in a first chute 3 into the tablet container 6, tablets dispensed into and accumulated in a second chute 3 are to be dispensed first, the following steps may be performed. Initially, the barcode on the tablet container 6 into which the tablets from the second chute 3 are to be dispensed is scanned. Then, once the barcode is scanned, the LEDs on the first chute 3 are turned off, the solenoid connected to the first chute 3 is driven, and the gate plate 26 of the first chute 3 is locked so as to be maintained at the closed position. This prevents the possibility of accidentally dispensing the tablets from the first chute into the tablet container 6. However, preferably, in order to reflect that tablets are being dispensed into the first chute 3, a different color LED is lit up, for example, to alert the operator.

b. Troubleshooting

In the event that tablets become jammed in a tablet cassette 2 or have run out during the tablet dispensing operation, the liquid crystal monitor 8 identifies the jammed or depleted tablet cassette 2 or the LEDs provided on the relevant tablet cassette 2 become lit. For example, the background of the liquid crystal monitor 8 may be displayed in red to facilitate identification of the relevant tablet cassette 2. In this case, it is preferable that the method by which an operator is alerted of jamming of tablet in a tablet cassette 2 is different from the method by which an operator is alerted of a tablet cassette 2 that has run out of tablets. Further, a tablet jam can be detected based on the state of conduction to the motor 20, the rotating state of the output shaft of the motor 20, and so on, while a lack of tablets can be detected based on the detection signal from the tablet detection sensor. This allows the operator to immediately identify the tablet cassette 2 in question and address the problem. Alternatively, through touch operation of the area on the liquid crystal monitor 8 for the relevant tablet cassette 2, the dispensing information screen, as shown in FIG. 13 is displayed. The dispensing information screen then displays a "reset" button 43 or the like so that the necessary processes are performed.

c. Prescription Cancel

In the event that a tablet dispensing operation is cancelled midway through the dispensing process, such as when a signal to cancel a prescription is input, the rotation of the rotor 13 is stopped, and the LEDs on the chute 3 in which the tablets to be dispensed have accumulated become illuminated. In the same manner as above, the operator can then dispense any accumulated tablets from the chute 3 into the tablet container 6. Next, the liquid crystal monitor 8 displays a "completion" button, showing that the prescription cancel has been completed and, through touch operation of this button, the prescription cancel process may be completed.

d. Consecutive Dispensing of the Same Type Tablets

In cases where the same type of tablets is to be consecutively dispensed, tablets cannot be dispensed from a tablet cassette 2 into a chute 2 if the tablets previously dispensed from the tablet cassette 2 have accumulated in the chute 3. Thus, the operation of the tablet cassette 2 is suspended until the tablets are dispensed from the chute 3 to the tablet container 6, and the liquid crystal monitor 8 displays that such an effect has taken place. In this case, preferably, the liquid crystal monitor 8 indicates certain information, such as a notice that tablet dispensing from that particular tablet cassette 2 is in a standby state, as well as other information such as number of tablets being dispensed. Thus, the possibility of mistakenly dispensing the tablets into a different tablet container 6 is prevented.

e. Tablet Collecting Process

In the event that electric power is not supplied because of power outage, etc. and the device is stopped, a tablet collecting process is performed as follows.

At the time of a power outage, tablets may have been dispensed into each chute 3 based on the inputted prescription data. Thus, when the device is stopped in this state, the data in the device side about the dispensed tablets is lost although the tablets have already dispensed into the chute 3. This makes impossible for the device to continue the process from the state before it is stopped after power supply is returned.

In this case, it is necessary to manually collect the tablets which have already dispensed into each chute 3. An initialization required screen is displayed on the liquid crystal monitor 8. When an initialization button is touched, the locked state of all chutes 3 is removed and the screen is changed to an initialization completion screen. Tablets dispensed from the chute 3 are collected. When collecting operation is finished and an OK button is touched on the initialization completion screen, the tablet collecting process is finished. However, in the case that tablets dispensed to the chute 3 are remaining, an alarm is displayed on the initialization completion screen. The background of the cassette display 41a corresponding to the chute 3 having remaining tablets is displayed as red. Moreover, the LED of each chute 3 is blinked. This makes it possible for a user to easily judge at a glance which chute 3 has tablets remaining As seen above, even when the device is returned from the stop due to power interruption, it is possible to judge which chute 3 has tablets remaining at a glance, such that the collecting process of tablets can be easily performed. Thus, tablets do not remain in the chute 3. Restart of the device can be smoothly performed. When tablets prescribed after that are dispensed, the occurrence of trouble, quantity error, etc. are prevented.

f. Recommended Bottle Size Display Process

Figure 29:
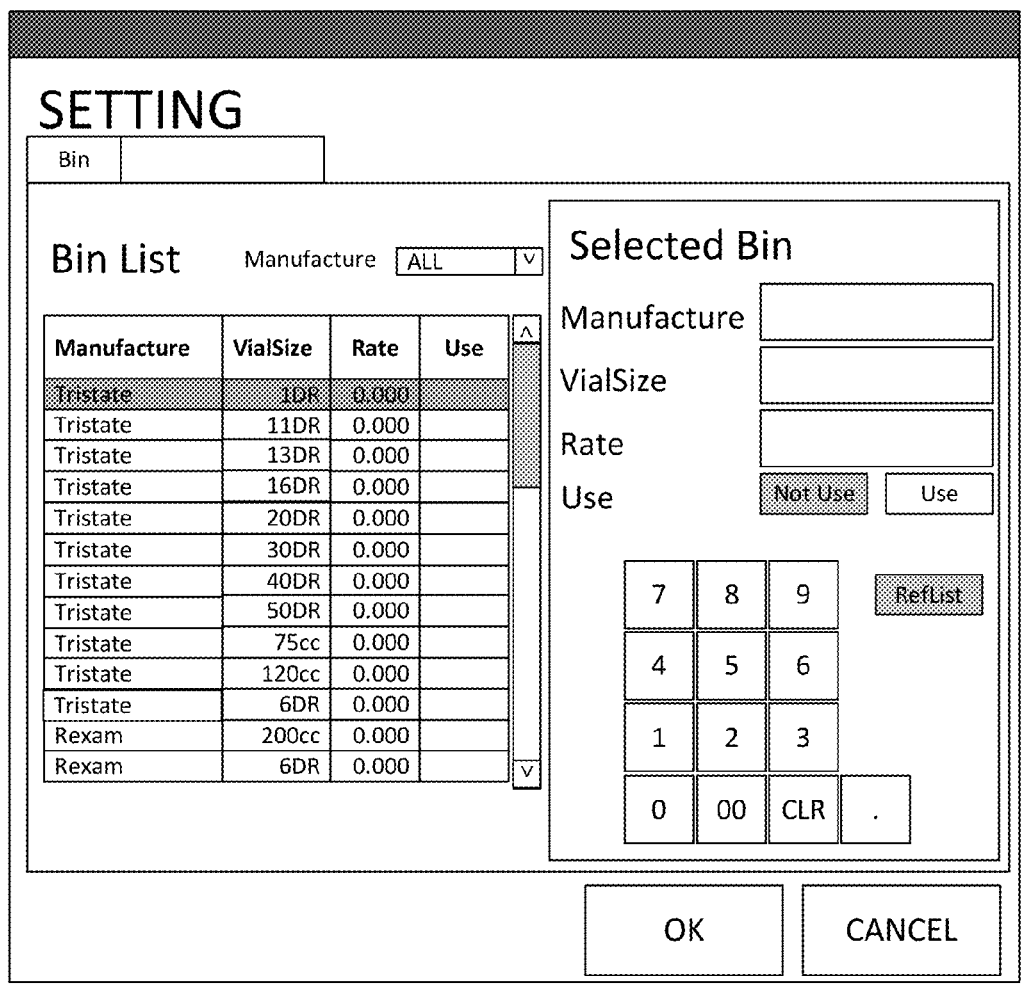
FIG. 29 is a list chart which is memorized in the memory of the control unit of FIG. 9 and shows the ratio of maximum number of tablets to be accommodated in the vial bottle.

The maximum number of tablets which can be respectively accommodated in each size of tablet containers 6 (vial bottles) used in the device is memorized in the memory of the control unit 5. For example, in the list shown in FIG. 29, in the case that the maximum number of tablets A which can be accommodated in the vial bottle which size is 20DR is 100 tablets, the rate is determined at 1 and the 20DR vial bottle becomes a standard tablet container. A 30DR vial bottle is memorized as having a rate of 1.5 and the maximum number of tablets is 150 compared to the 20DR vial bottle. A 40DR vial bottle is memorized as having a rate of 2 and a maximum number of tablets is 200.

A vial bottle to be dispensed is determined according to the dispensed number of a tablet (for example, tablet A) included in the prescription data as follows. That is, the range of tablet number to be accommodated by a vial bottle is related to each size of a vial bottle. The selection of a size of a vial bottle is determined according to which range the dispensing number belongs to. Specifically, for example, when the dispensing number N is N<100, the determined size of the vial bottle is 20DR, and when N is 100.ltoreq.N<150, the size is 30DR, and when N is 150.ltoreq.200, the size is 40DR. The determined size of the recommended bottle is displayed on the liquid crystal monitor 8. Thus, a user may prepare the corresponding vial bottle according to the size which is automatically determined based on the prescription data and displayed. As a result of this, he or she can perform the dispensing operation of tablets efficiently. In addition, when the dispensing number is over 200 tablets, it is possible to inform error or perform a division process as described below. With respect to another tablet, tablet B or C, etc. which is a different type from tablet A, the maximum number of tablets which can be accommodated in the 20DR tablet container 6 or the ratio to the maximum number of tablets A may be memorized. In the case of the latter, a vial bottle is determined in accordance with the ratio memorized. Furthermore, when there is no stock of the vial bottle having the corresponding size, one larger size vial bottle can be automatically selected based on the stock information.

g. Shop Adoption Bottle Registration Process

The manufacturer and/or size of a vial bottle which a shop adopts is different. However, to register the maximum number of all types of tablets respectively for each size vial bottle of each manufacturer is problem such that it requires great care because of the enormous number. In the case that a vial bottle or a tablet is newly registered, the same problem is occurs. Thus, in the first preferred embodiment, to solve this problem, the maximum number of tablets compared to the standard tablet container is memorized in master data. With respect to another vial bottle (not only the different size vial bottle of a same maker, but also several size vial bottle of other makers), the ratio of each vial bottle against this value is memorized. The maximum number of the other vial bottles is calculated by multiplying the maximum number of tablets of the standard tablet container by the ratio in accordance with the kind of tablet to be accommodated. This eliminates the need for memorizing the maximum number of each tablet to the other vial bottle and can omit troublesome time and effort to register and further can flexibly respond to a vial bottle or tablet registered newly.

h. Division Prescription Process

In the case that dispensing number of a tablet included in a prescription data can not be accommodated in a single vial bottle, the tablets are divisionally prescribed by dividing the tablets into several vial bottles.

Figure 30:
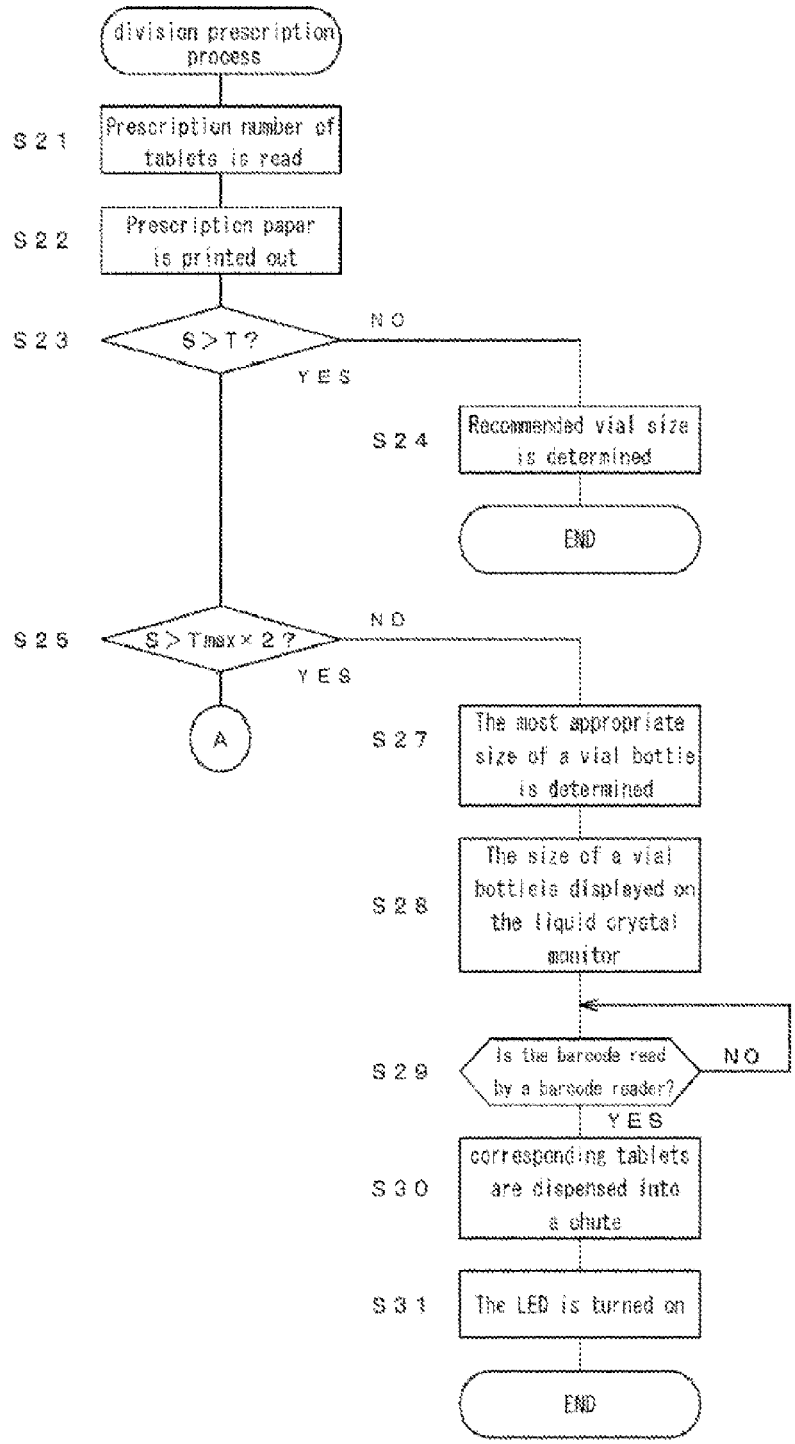
FIG. 30 shows a flowchart showing the content of the division prescription process according to the first preferred embodiment.
Figure 31:
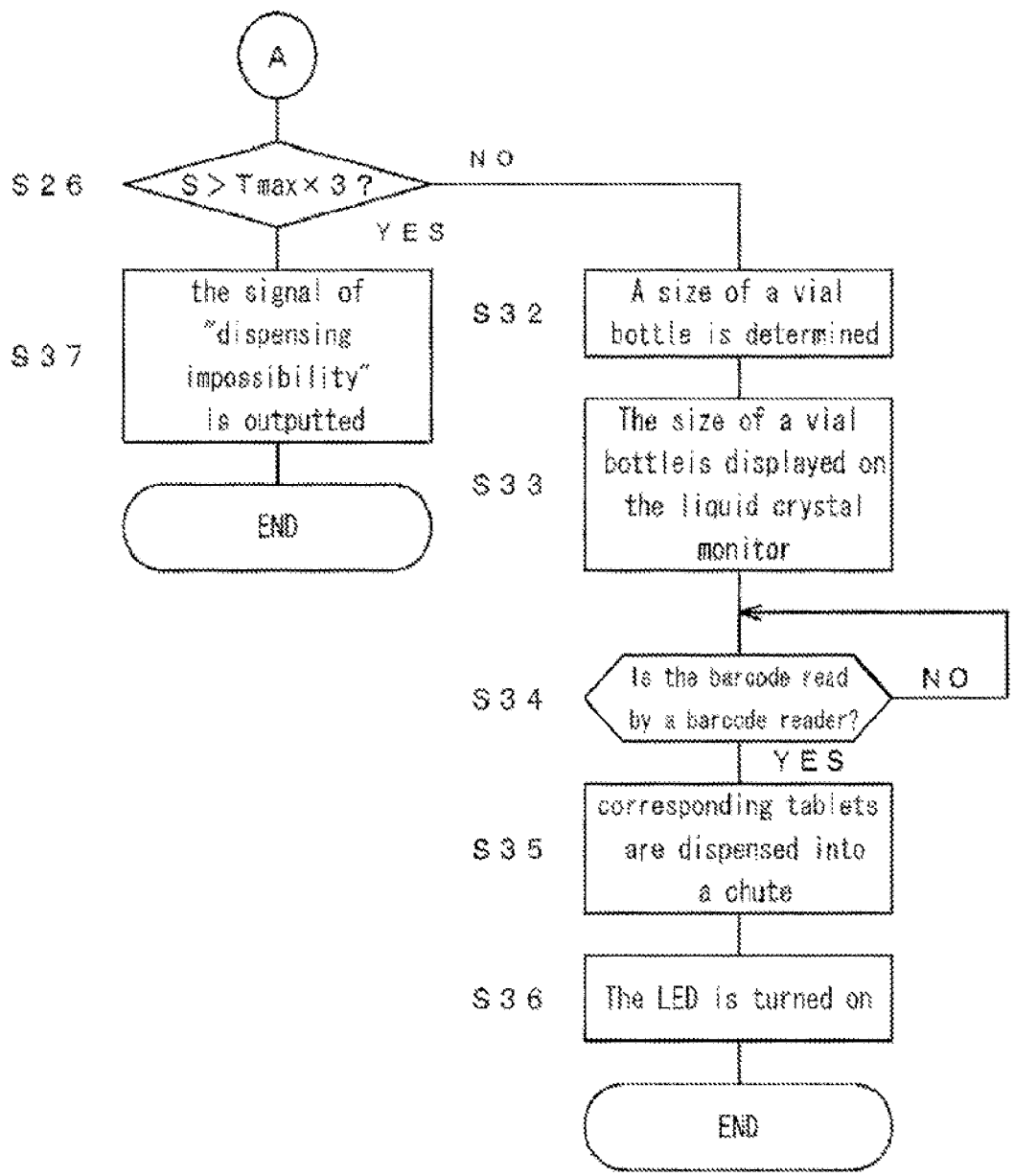
FIG. 31 shows a flowchart showing the content of the division prescription process according to the first preferred embodiment.

As shown in flowcharts of FIGS. 30 and 31, firstly, the prescription number of tablets (the number of tablets prescribed) is read (step S21) and the prescription paper is printed out (step S22).

It is judged whether or not the prescription number S of tablets is more than the tablet number Tmax which can be accommodated in the largest vial bottle (step S23). If the prescription number S is less or equal to the maximum number of tablets Tmax, the recommended vial size is determined based on the prescription number in the same manner as the above (step S24). In the event that the prescription number S is over the maximum number of tablets Tmax, it is further judged whether or not the prescription number is more than two times as large as the maximum number of tablets (step S26).

In the event that the prescription number S is less than or equal to twice as large as the maximum number of tablets, the most appropriate size of a vial bottle is determined based on the prescription number. Herein, the size of a vial bottle is determined based on the value which is obtained by dividing the prescription number in the same manner as the step S22. If the size of a vial bottle is determined, that effect is displayed on the liquid crystal monitor 8 (step S28). If the barcode printed on the prescription paper is read by a barcode reader (step S29), corresponding tablets are dispensed into a chute 3 (step S30). In this case, if the same tablets are accommodated into several tablet cassettes 2, the tablets may be dispensed from the two of them respectively. Further, if the same tablets are accommodated in only one tablet cassette 2, firstly, the divided tablet number may be dispensed from it, and the LED of the chute 3 dispensing the tablets is turned on (step S31). In this case, it is preferably to blink the LED twice so as to inform that it is divided into two. Furthermore, if the twice blinking is performed with respect to each predetermined time, a user will not miss it. It is preferably to display such that a user can identify the difference between in the case of dispensing tablets to two points and in the case of dispensing tablets to one point (for example, it is preferably to change a color of the display, etc.). In the case of dispensing tablets to two points, it is necessary to collect from each chute 3 by using two vial bottles. In the case of dispensing tablets to one point, it is only necessary to dispense a half of the rest tablets to the chute 3 again after it is finished to collect a half of the prescription number of the tablets dispensed from the chute 3. At this time, it is preferably to inform that the operation for collecting a half of the rest tablets remaining by blinking an LED one time (It is preferred to blink an LED with respect to each predetermined time.).

In the case that the prescription number of tablets is less than or equal to three times as large as the maximum number of tablets, a size of a vial bottle is determined based on the obtained value as well as the step S26. After a size of a vial bottle is determined, a process similar to the case of dividing tablets into two is performed. In addition, when tablets are dispensed from the same tablet cassette 2 to the chute 3 (in the case of dispensing tablets to one point), the division number may be displayed as the lighting a number on an indicator provided on the chute 3. This enables a user to recognize the division number at a glance. The lighting number of the indicator may be decreased every time tablets are dispensed into a vial bottle. This enables a user to recognize the remaining number of the collecting operation for a vial bottle. In addition, when tablets are divided into two or three, a number corresponding to the division number may be lighted at the indicator of the cassette display 41*a*.

In the case that the prescription number is more than three times as large as the maximum number of the accommodated tablets, the signal of "dispensing impossibility" is outputted (step S37), and after the process is finished.

This makes it possible to dispense tablets divided into several vial bottles and respond flexibly even when a lot of tablets are needed to be dispensed, when the division prescription is available. Although tablets are divided into three or less in the above example, it is possible to divide tablets into four or more. Furthermore, the division prescription may be utilized to enable tablets to dispense into a vial bottle whose size is small when a part size of vial bottles is missed.

i. Other Embodiments

Figure 15:
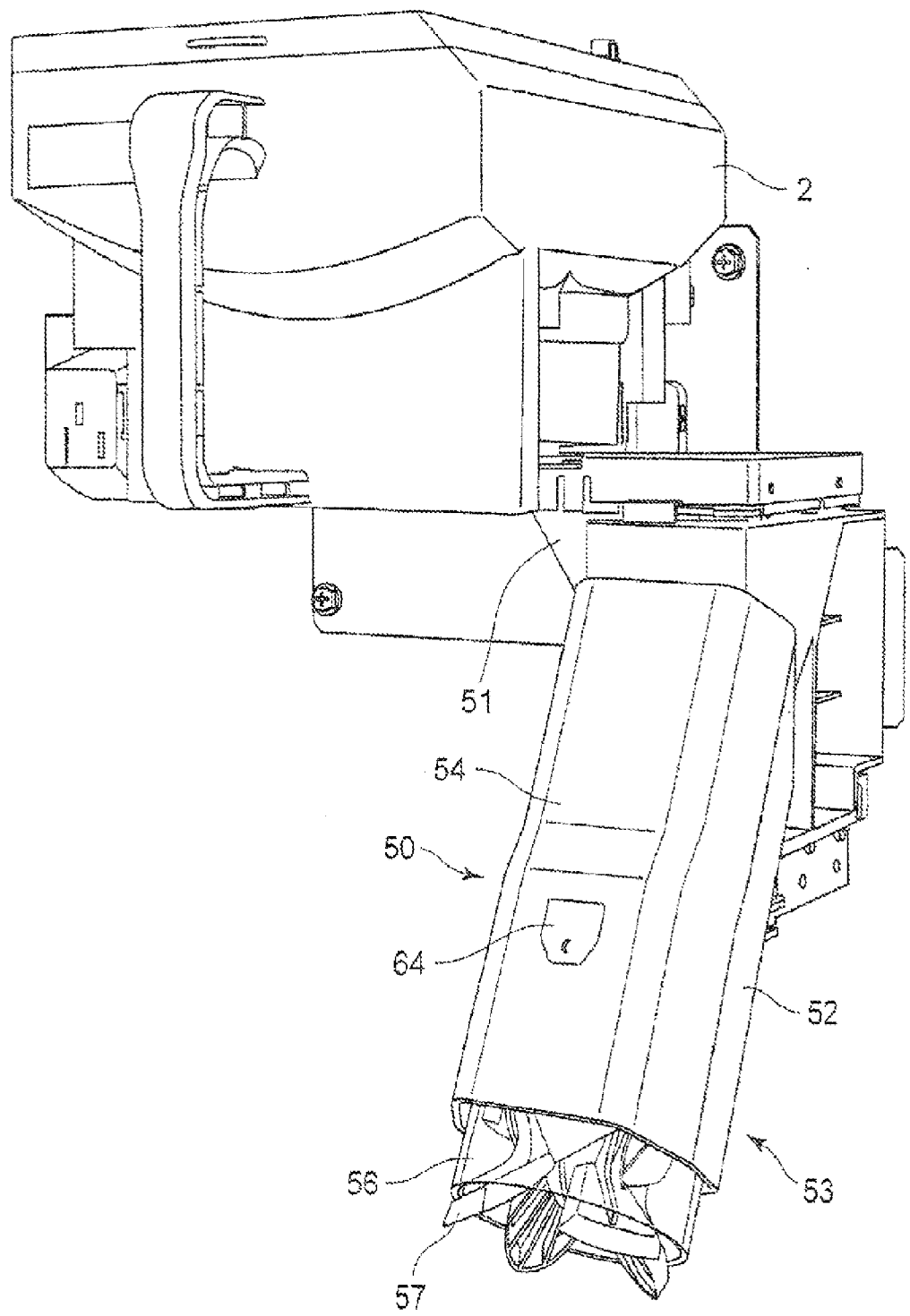
FIG. 15 is a perspective view of one set of the tablet cassette and chute according to a second preferred embodiment.
Figure 16:
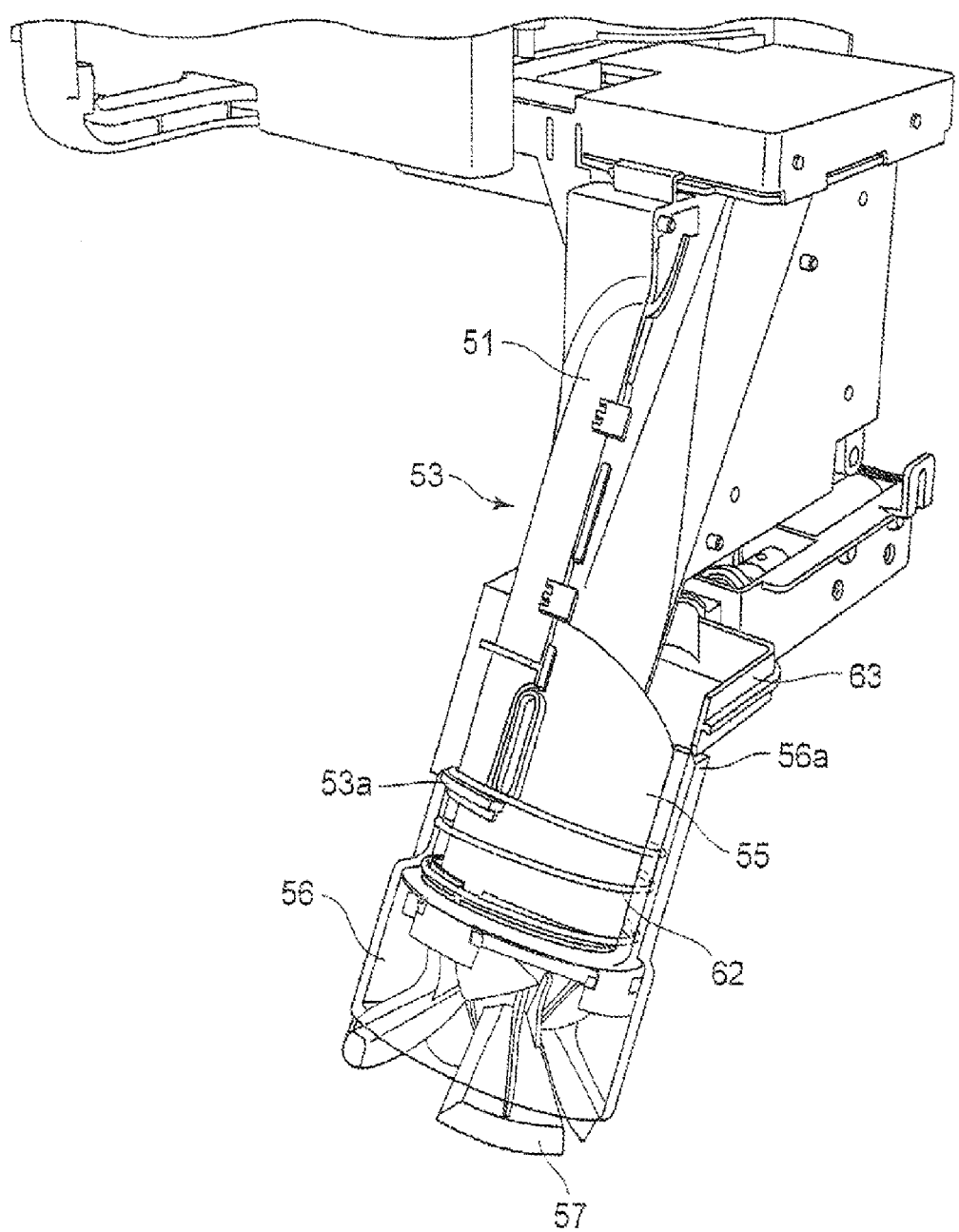
FIG. 16 is a perspective view showing the chute of FIG. 15 with the tubular guide removed.
Figure 17:
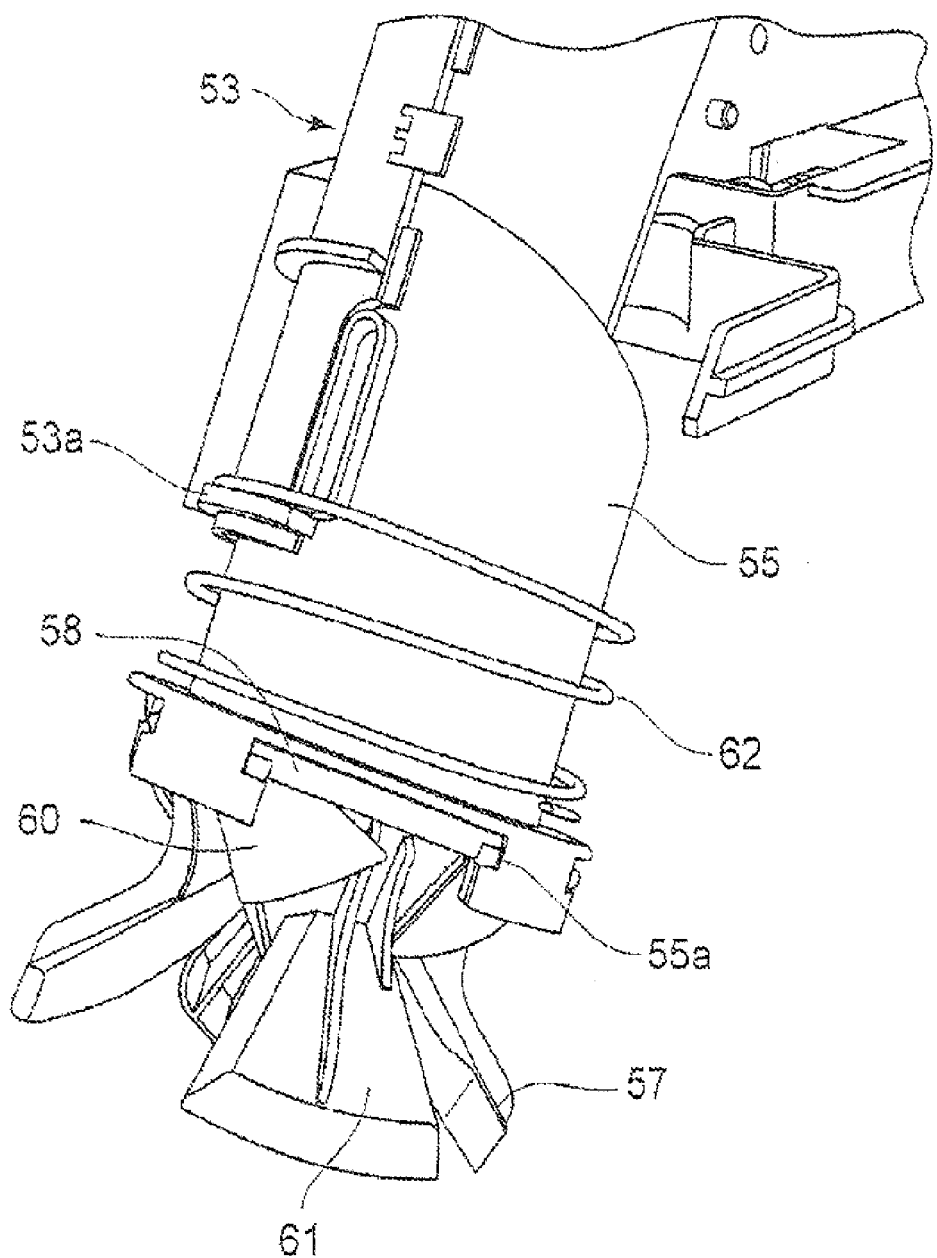
FIG. 17 is a perspective view showing the chute of FIG. 16 with the nozzle case also removed.

The present invention is not limited to the configuration disclosed in the above described first preferred embodiment, and various modifications are possible. For example, each chute 50 can be configured as shown in FIGS. 15 through 17. More specifically, each chute 50 comprises a guide path 53 on its front surface. The guide path 53 is divided into left-hand and right-hand components, such that the guide path 53 is formed by a first case 51 and a second case 52. The guide path 53 projects obliquely downward toward the front, and at least the front surface thereof is made of a translucent material. Further, the guide path 53 may be marked with lines indicating the number of tablets accommodated in the chute 50. Unlike the above-described first preferred embodiment, the guide path 53 has a uniform cross-sectional area, such that the cross-sectional area of the lower portion of the guide path 53 is the same as the upper portion.

Figure 18:
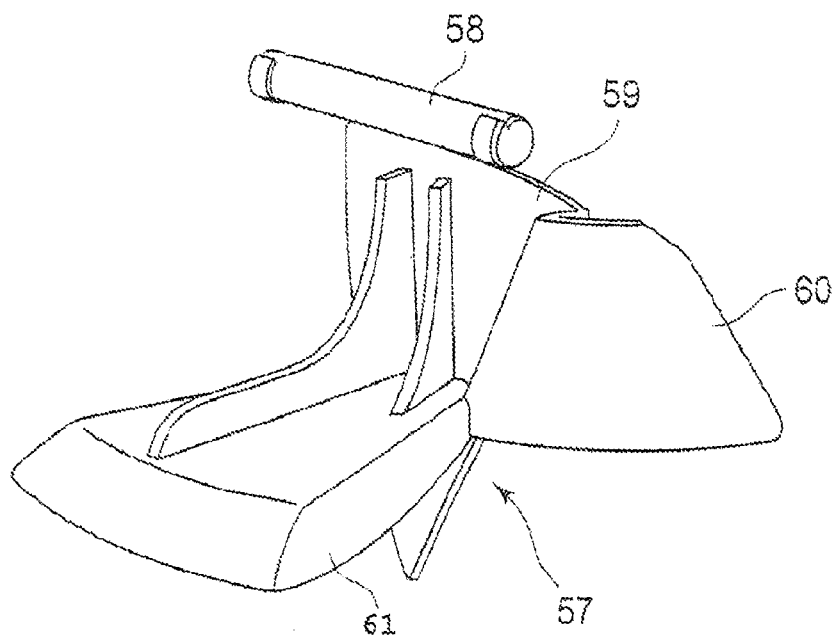
FIG. 18 is a perspective view of the nozzle plate shown in FIG. 15.
Figure 19:
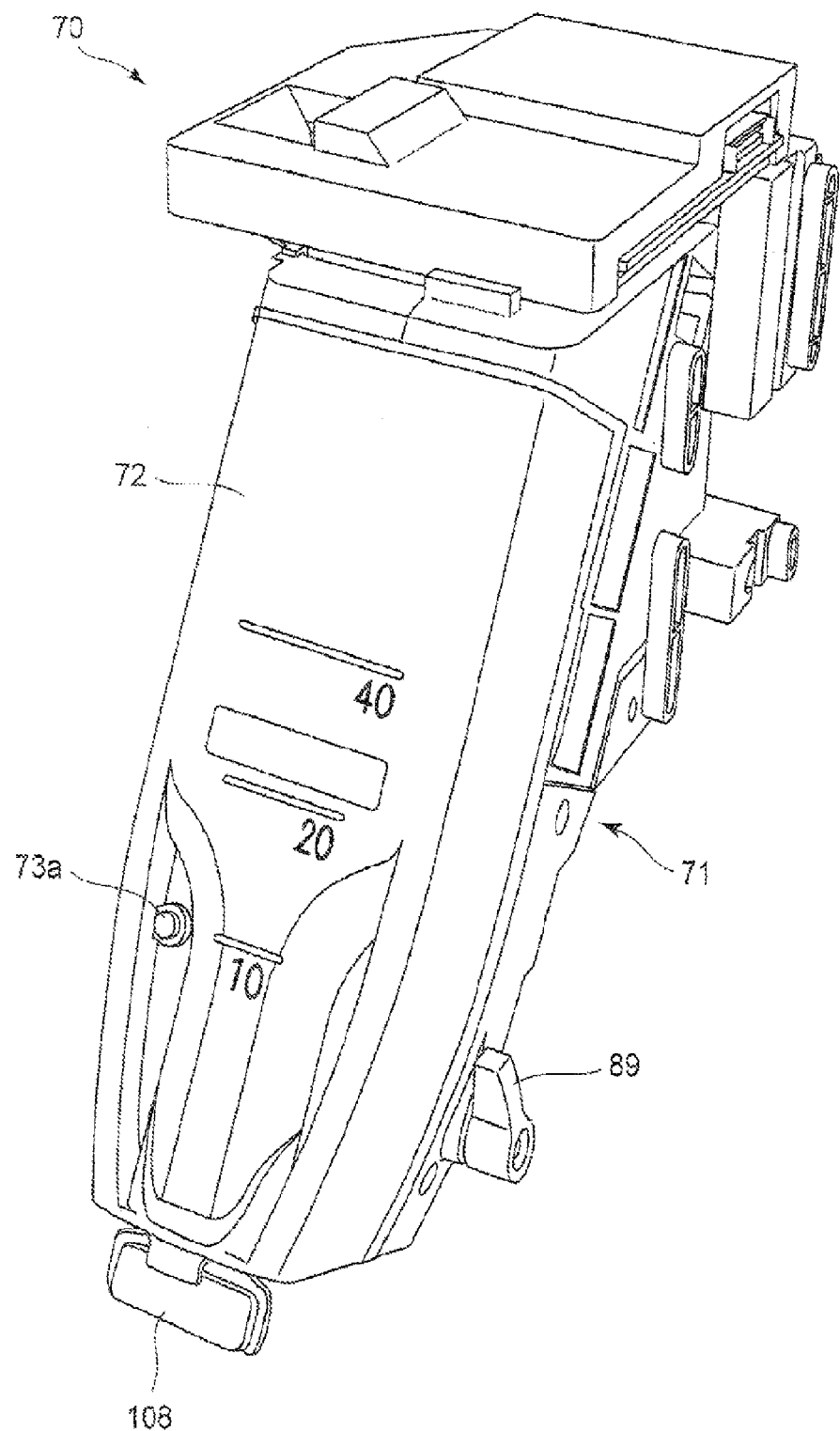
FIG. 19 is a perspective view of the chute according to a third preferred embodiment.

A tubular guide 54 is attached to the outer periphery of the guide path 53 and at least the front side of the tubular guide 54 is translucent. Further, a lock ring 55 is attached to the inside of the guide path 53 and a nozzle case 56 is disposed such that it may move vertically. The nozzle case 56 comprises a gate member made up of a plurality of plates 57 radially biased inwardly toward each other. As shown in FIG. 18, each plate 57 comprises a shaft 58, a closing piece 59 extending from the shaft 58 and having a roughly triangular shape, a guide piece 60 extending from the closing piece 59 in the lateral circumferential direction, and a pressure receiver 61 extending from the external side of the closing piece 59 outwardly in a radial direction.

The plates 57 are arranged on the inner peripheral side of the lock ring 55, and the shaft 58 is rotatably supported by an inner peripheral bearing 55*a* of the lock ring 55. Further, the lock ring 55 is elastically supported by a coil spring 62 provided between the lock ring 55 and the leading end flange 53*a* of the guide path 53. In a first position, the plates 57 contact each other to cover the opening of each chute 50. Specifically, in the first position, the plates 57 are configured such that the exterior surfaces of the pressure receivers 61 abut the opening edge of the lock ring 55 and rotate around the shaft 58 inwardly, causing the outer edges of the closing pieces 59 to abut one another. Thus, the lower end opening of the chute 50 is closed. When a force is applied to a surface of the plates 57, the plates 57 may be placed in second position by moving radially outwardly away from each other. In the second position, the opening of each chute 50 is exposed.

A portion of the nozzle case 56 extends upward along the outer periphery surface of the guide path 53, and a lock receiver 56*a* is formed at the leading end thereof. The lock receiver 56*a* is configured so that the rod 63 of the solenoid (not shown) provided on the rear side of the chute 50 can lock therewith or detach therefrom. When locked, the upward movement of the lock ring 55 is obstructed so as to prevent the closing pieces 59 of the plates 57 from separating from each other and exposing the lower end opening of the chute 50.

In a second preferred embodiment, when a prescribed number of tablets are dispensed into the guide path 53 of the chute 50 based on prescription data, the red LED provided on the chute 50 is illuminated. Then, when a barcode scanner scans the barcode attached to the tablet container 6 (not shown) having a size corresponding to the number of the tablets accommodated in the guide path 53, the blue LED (display 64) provided on the chute 50 blinks, the solenoid is driven so as to cause the rod 63 to detach from the lock receiver 55*a* of the lock ring 55, and the locked state of the nozzle plates 57 is released.

When the open end of the tablet container 6 is placed at the opening at the lower end of the chute 50 and pushed in an upward direction against the exterior surfaces of the pressure receivers 61, the nozzle plates 57 move and push the lock ring 55 up against the impelling force of the coil spring 62, causing the pressure receivers 61 of the nozzle plates 57 to expand outwardly. As a result, the closing pieces 59 separate from one another, and the tablets accumulated in the guide path 53 are discharged into the tablet container 6. At this time, the closing pieces 59 expand inside the tablet container 6, and the tablets are smoothly discharged into the tablet container 6. Further, while expansion of the nozzle plates 57 creates a gap between the adjacent closing pieces 59, because the guide pieces 60 are positioned at such gaps, the tablets do not fall outside of the tablet container 6.

Thus, according to the chute 50 shown in FIGS. 15 through 18, the tablet container 6 is pushed in an upwardly direction against the nozzle plates 57, and specifically against the pressure receivers 61, such that the closing pieces 59 separate from each other to expose the lower end opening of the chute 50 in accordance with the size of the opening of the tablet container 6. As such, tablets may be dispensed from the chute 50 into the tablet container 6. Accordingly, even though the openings of tablet containers 6 may vary in size, such a configuration ensures that the degree of exposure of the lower end opening will be suitable for the size of the container, ensuring that tablets do not fall out and that dispensing speed is not slowed. Further, because the guide path 53 is formed with a uniform cross-sectional area, simply opening the nozzle plates 57 ensures that all tablets will be dispensed into the tablet container 6 without any remaining tablets in the guide path 53.

Additionally, in a third preferred embodiment, the configuration of the chute 3 may be configured as a chute 70 having a configuration attachable to and detachable from the front surface side of a chute body 71 as shown in FIGS. 19 through 25 instead of the configuration of the first preferred embodiment.

Figure 20:
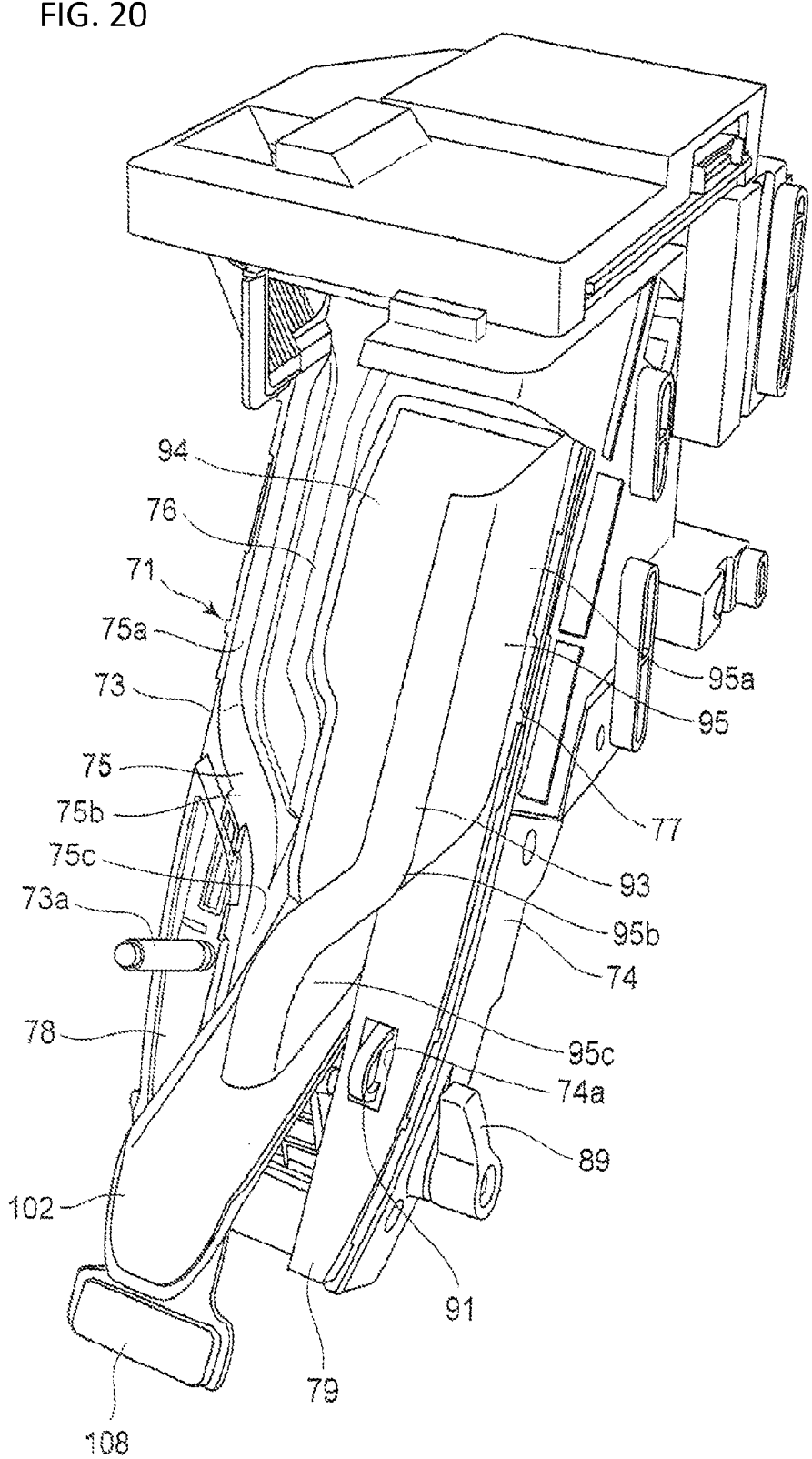
FIG. 20 is a perspective view showing the chute of FIG. 19 with the caver removed.
Figure 21:
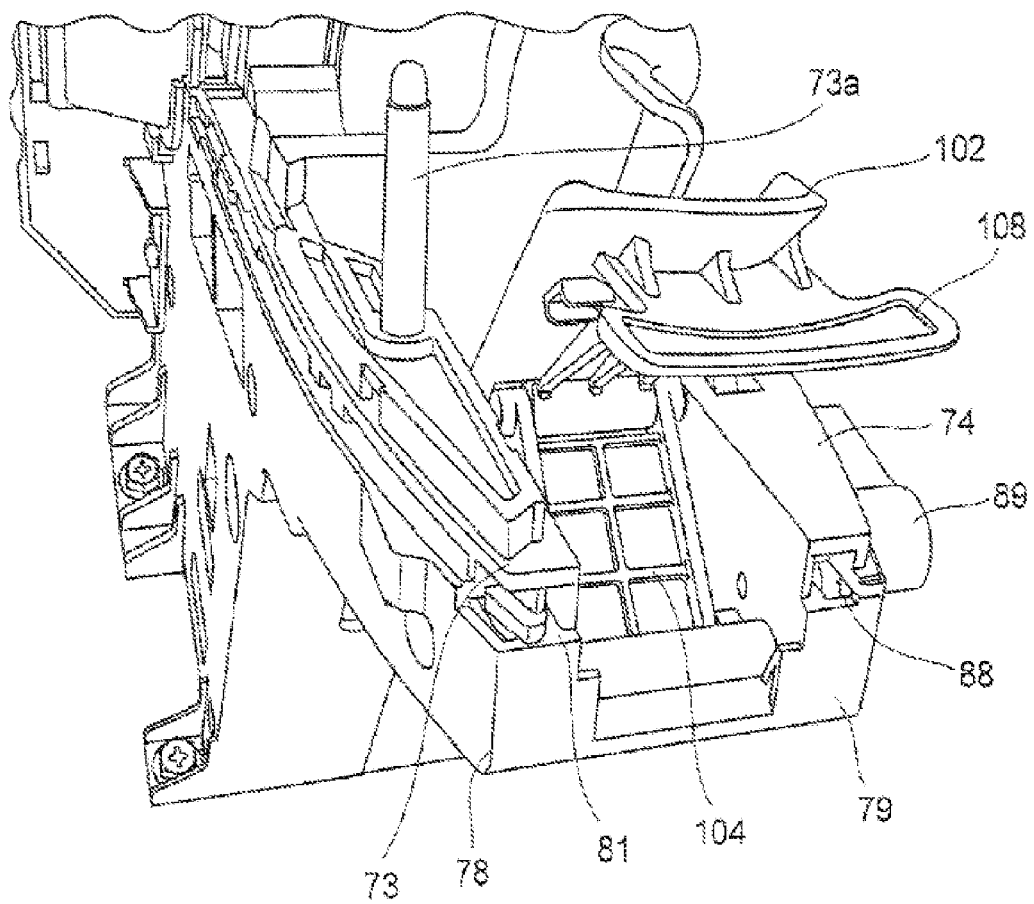
FIG. 21 is an enlarged perspective view of the lower end side of FIG. 20.

As shown in FIGS. 20 and 21, the chute body 71 is composed of a first half portion 73 and a second half portion 74. An interior surface of a side wall of the first half portion 73 is composed of a body side first guide wall 75 gradually expanding from a middle part to inside of it. The body side first guide wall 75 is composed of a series of a first straight line portion 75*a*, a curvature portion 75*b* and a second straight line portion 75*c*. A convex portion is formed in the further inside of the body side first guide wall 75. An inside surface of a side wall of the second half portion 74 is gradually expanded from a middle portion to inside of it and composed of a body side second guide wall 77 guiding the side surface of the slide plate 93. A second auxiliary member 78 is attached to a lower portion of the second half portion 73 respectively.

Figure 25:
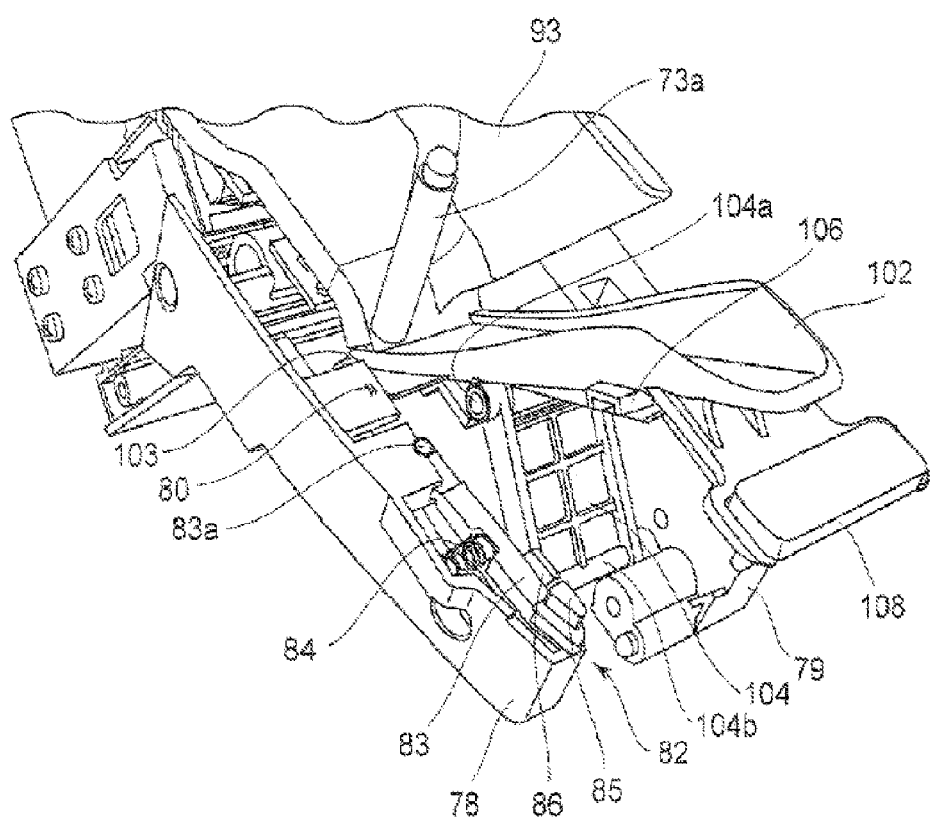
FIG. 25 is a partial perspective view showing the chute of FIG. 19 with the first half portion and the second half portion removed.

As shown in FIG. 25, a LED 80 is placed between the first half portion 73 and the first auxiliary member 78. The LED 80 lights in a state that the cover 72 is attached to the chute body 71 and the lower opening portion of it is closed by a gate plate 102 as described below. Thus, when a dispensing preparation of tablets to the chute 70 is completed, the LED lights. Furthermore, when tablets are dispensed, the LED 80 blinks and it is informed to be able to collect tablets by the tablet container 6 (not shown in FIGS. 19-25).

As shown in FIG. 25, a first engagement hole 81 is formed in a lower portion composed of the first half portion 73 and the first auxiliary member 78. A lock mechanism 82 is provided in the first engagement hole 81. As shown in FIG. 25, this lock mechanism 82 comprises a rotatable piece 83 provided to pivot around a support axis 83a and a coil spring 84 biasing this rotatable piece 83. A click portion 85 is formed at the top of the rotatable piece 83 and a locking projecting portion 86 is formed at the side edge of a middle portion. The click portion 85 is pushed by a first engagement projecting portion 110 (described below) of a cover 72 inserted into the first engagement hole 81. The engagement projecting portion 86 engages with and detaches from an engagement receiver 106 of a gate plate 102 as described below. The coil spring 84 biases the gate plate 102 in the direction to maintain a state that the engagement projecting portion 86 engages the engagement receiver 106. When the cover 72 is attached to the chute body 71 and the click portion 85 is pushed to the first engagement projecting portion 80 so that the rotatable piece 83 rotates against the biasing force of the coil spring 84, the engagement projecting portion 86 is parted from the engagement receiver 106. In addition, a taper surface is formed at the under surface of the tip of the engagement projecting portion 86, so that it smoothly engages with the engagement receiver 106 of the gate plate 102. Furthermore, an axis-like guide portion 73a which guides the light from the LED 80 is formed at the front surface of the first half portion 73.

Figure 23:
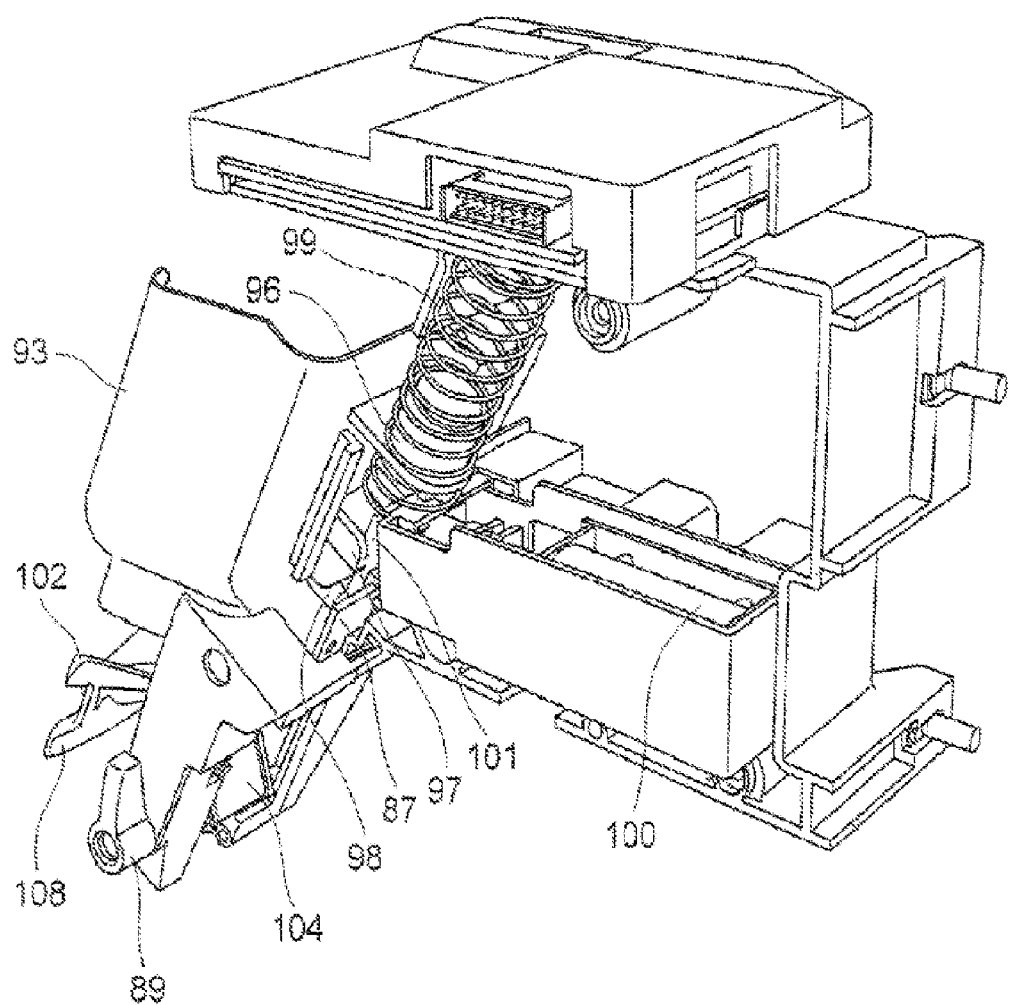
FIG. 23 is a perspective view showing the chute seen from the opposed side of FIG. 21.
Figure 24:
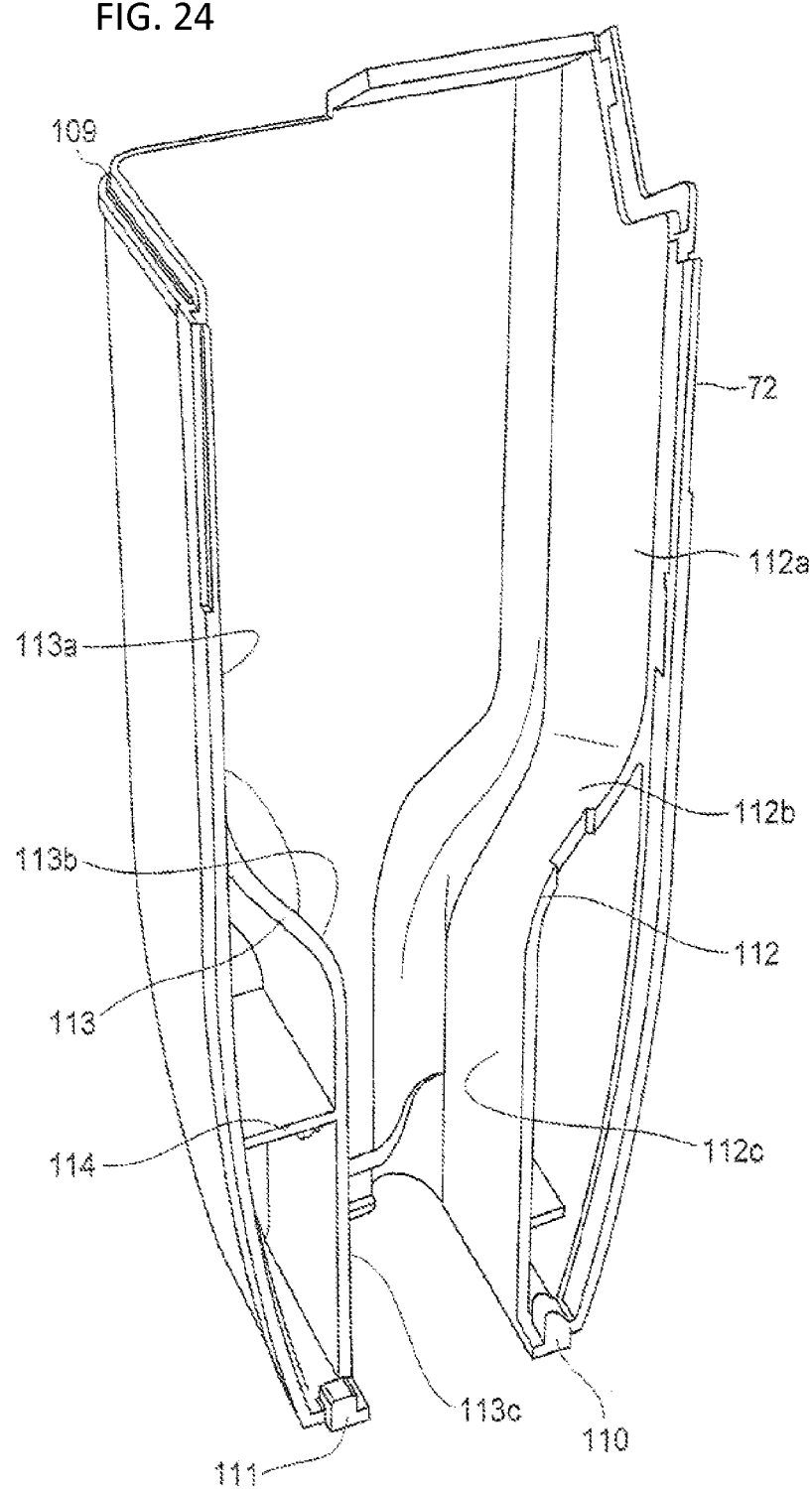
FIG. 24 is a perspective view showing the caver seen from the opposed side of FIG. 19.

As shown in FIG. 23, a detection sensor 87 is provided between the second half portion 74 and the second auxiliary member 79. The detection sensor 87 detects a detected portion 98. The detected result is utilized to judge whether or not the slide plate 93 is positioned at the upper position (the closure position of the gate plate 102).

Figure 22:
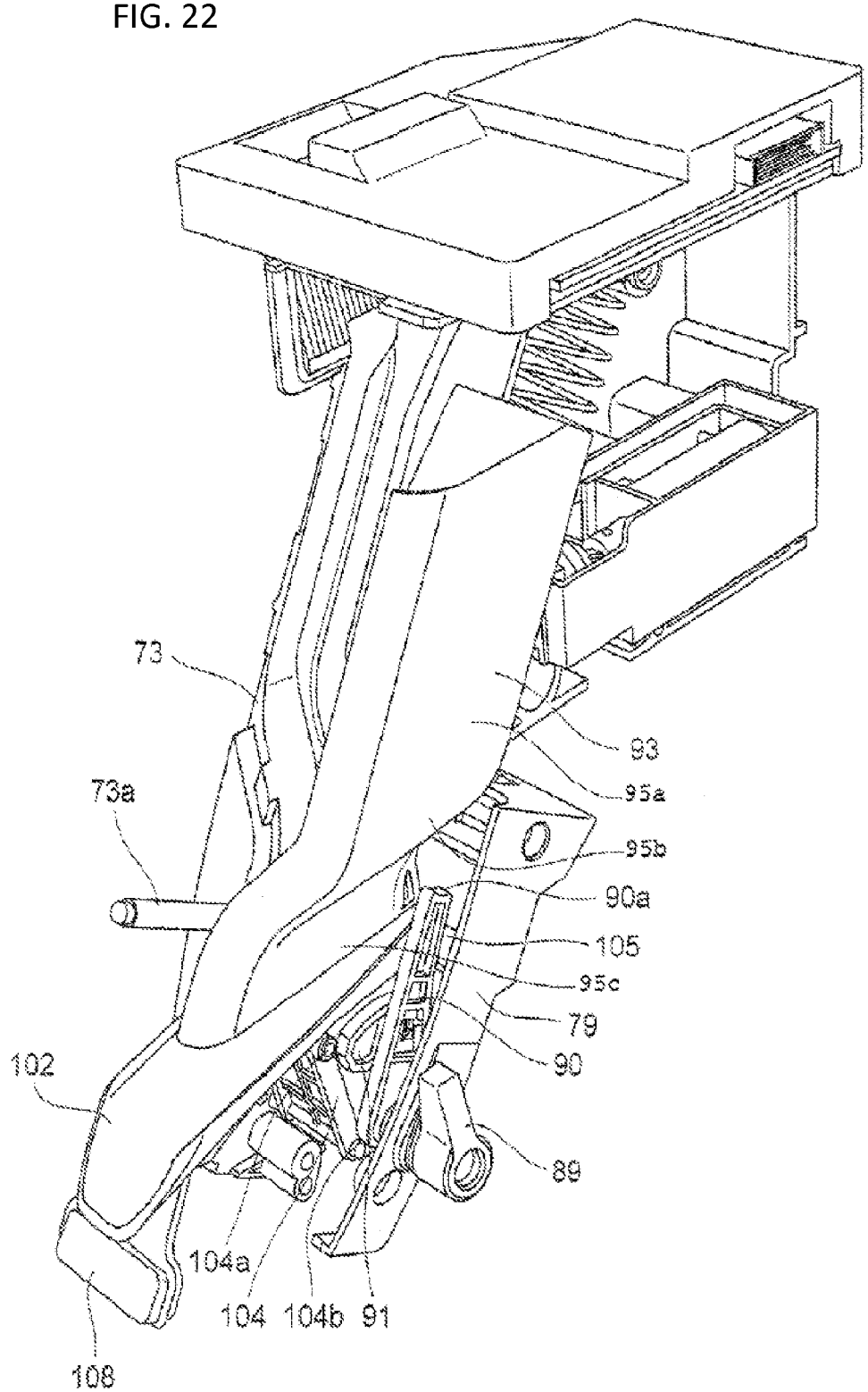
FIG. 22 is a perspective view showing the chute of FIG. 20 with the second half portion removed.

As shown in FIG. 21, a second engagement hole 88 is formed at the lower portion composed of the second auxiliary member 79 and the second half portion 74. A knob 89 is placed rotatably at the outside surface of the second auxiliary member 79. As shown in FIGS. 21 and 22, the rotation axis of the knob 89 projects into the interior space of the second half portion 74 and an arm portion 90 is fixed therein. As shown in FIG. 20, a locking piece 91 which projects from and enter into the second half portion 74 via a notch 74a formed in the second half portion 74 is fixed at the middle portion of the arm portion 90. A tip side edge portion of the arm portion 90 comes into contact with a projecting portion 105 of a gate plate 102 as described below, so that this gate portion 102 can open and close. Further, a recess 90a is formed at the tip of the arm portion 90. This recess 90a engages with and detaches from the projecting portion 105 of the gate plate 102 and positions the gate plate 102 at the opening position in a state of engaging. A rectangular-like opening (not shown) is formed at the center of the division wall of the chute body 71 composed of the first half portion 73 and the second half portion 74 and a solenoid 100 is provided at a space at the back side of the chute body 71 as shown in FIG. 23.

As shown in FIG. 20, the slide plate 93 comprises a first guide wall 94 of the back side and a second guide wall 95 of the second half portion 74 side. Here, the staging portion according to the embodiments of the present invention includes a first guide wall 94 and a second guide wall 95.

As shown in FIG. 23, a cylindrical spring receiver 96 extending upward along back surface of the body side first guide wall 94, a locking receiver 97 projecting in a roughly U-shaped form in the direction of the back surface and a detected portion 98 cylindrically projecting in the direction of the back surface are formed respectively in the body side first guide wall 94. The spring receiver 96, the locking receiver 97 and the detected portion 98 project into the space of the back side via a opening formed in the chute body 71. A coil spring 99 provided between the spring receiver 96 and the upper surface comprising the back side space of the chute body 71 is placed at the spring receiver 96. The slide plate 93 which receives the biasing force from this coil spring 98 comes contact with the convex portion formed in the first half portion 73 of the chute body 71 by the side edge portion of the first guide wall 94 and is positioned at the lower position where the outer surface of the second guide wall 95 comes contact with the interior surface of the second half portion 74. A rod 101 of a solenoid 100 is engaged with and detached from the locking receiver 97. When the slide plate 93 is positioned at the upper position, the detected portion 98 is detected by the detection sensor 87.

As shown in FIG. 20, the body side second guide wall 95, referred herein as the staging portion, is formed as a figure along the inside surface of the side wall of the cover 72 and the second half portion 74. That is, the second guide wall 95 is composed of a first straight portion 95a, a curved portion 95b continued from the lower side of the first straight portion 95a and a second straight portion 95c further continued from the lower side of the curved portion 95b. The slide plate 93 goes up and down along the back surface of the chute body 71. In the case that the slide plate 93 is positioned at the lower position, a tablet passage is composed of the inside surface of the second guide wall 95, the inside surface of the side wall of the first half portion 73 and the front cover 72. For details, a wide passage is formed by the first straight portion 75a, 95a and a first straight portion 112a as described below. In the case that the slide plate 93 is positioned at the upper position, the second straight portion 95c goes from the opposed position of the first straight portion 75a, 112a to the opposed position of the curved portion 75b, 112b or the second straight portion 75c, 112c. In this state, the part which cross-sectional area of the passage becomes small is eliminated, so that it is possible to prevent tablets from being clogged. Further, a gate plate 102 is rotatably placed at the lower portion of the first guide wall 94. Here, a push-receiver 108, which will be described later, moves between the staging and dispensing positions in concert with the staging portion. As described above, the staging portion includes a first guide wall 94 and a second guide wall 95. Thus, the staging portion having the first guide wall 94 and the second guide wall 95 moves instead of the chute unit itself, and that makes the chute unit with a simple configuration. The chute unit will become larger and will need a more complex configuration, if the chute unit moves by itself. It also makes difficult to achieve an inexpensive and simple maintenance unit due to increasing of the replacement parts for the chute unit.

As shown in FIG. 25, the gate plate 102 has a half cylindrical shape, and the tip part of it gradually declines downward according to heading towards the tip. A rotation axis is formed at the upper portion of the gate plate 102. The rotation axis is connected to the lower portion of the first guide wall 94 of the slide plate 93. One end portion of the auxiliary plate 104 is rotatably connected to the center portion of the back side of the gate plate 102 via a pivot 104*a*. The other end portion of the auxiliary plate 104 is rotatably supported between the first half portion 73 and the second half portion 74 via a pivot 104*b*. This makes the slide plate 93 go up and down by pivot motion of the gate plate 102. In this embodiment, the gate member may include the gate plate 102.

As shown in FIG. 25, one end side of the rotation axis 103 of the gate plate 102, referred herein as the gate member, is composed of a projecting portion 105 projecting laterally. The projecting portion 105 is pushed by the tip portion of the arm portion 90 fixed on the knob 89. The projecting portion 105 is engaged with the recess portion 90*a* of the tip of the arm portion 90, so that the gate plate 102 is positioned at the open position. As shown in FIG. 25, a locking receiver 106 projects laterally from the edge of the back side of the gate plate 102. The locking receiver 106 is formed in a roughly U-shape, so that its rigidity is increased. A curved surface is formed on the upper surface of the locking receiver 106, so that a locking projecting portion provided at the chute body 71 is easily locked to the upper surface.

When the slide plate 93 is positioned at the lower position, the rotation axis of the gate plate 102 is limited to the lower side. This makes the gate plate 102 position to the close position where the lower portion of a tablet passage formed by the first half portion 73, the slide plate 93 and the cover 72 is closed. When the knob 89 is operated, the projecting portion 105 is pushed by the tip of the arm portion 90, so that the gate plate 102 is rotated from the close position to the open position. A push-receiver 108 projecting to the lower side than the lower portion is formed at the back surface of the tip side of the gate plate 102. This push receive portion 108 is pushed into by the upper opening of the tablet container 6 as well as the second preferred embodiment, so that the gate plate 102 is rotated from the close position to the open position. In this embodiment, the release member may include a push-receiver 108.

As shown in FIGS. 21-25, the cover 72 is formed in a groove shape, and made of a material having translucency. A shoulder 109 is formed at the upper end portion of the cover 72. The shoulder 109 engages with a receive portion in the side of the tablet cassette 2. A first engaging projecting portion 110 and a second engaging projecting portion 111 are formed at the both side of the lower portion of the cover 72. Each of engaging projecting portions 110, 111 is engaged with and detached from each of engaging holes 81, 88 formed on the chute body 71. When the first engaging projecting portion 110 is inserted to the first engaging hole 81, the click portion 85 of the rotatable piece 83 is pushed and the rotatable piece 83 is rotated against the biasing force of the coil spring 84. This enables the click portion 85 of the rotatable piece 83 to release the locking state to the locking receiver 106. Therefore, it is easily possible to judge whether or not the stored tablet number is adequate and to select the tablet container 6 to dispense stored tablets.

A cover side first guide wall 112 and a cover side second guide wall 113 which forms the space reducing its section area gradually according to heading toward the lower side are formed at the inside of the side wall of the cover 72 by the body side first guide wall and the body side second guide wall 77 of the chute body 71. The cover side first guide wall 112 and the cover side second guide wall 113 are composed of first straight portions 112*a*, 113*a*, curved portions 112*b*, 113*b* and second straight portions 112*c*, 113*c* in series from the upper side. A locking receiving wall 114 is formed between the side wall and the cover side second guide wall 113. A locking piece 91 provided to the arm portion 90 which is rotated by the knob 89 can be locked to the locking receiving wall 114. As described above, the shoulder 109 and the first engaging projecting portion 110 prevent the cover 72 from moving forward against the chute body 71. The locking state prevents the cover 72 from moving downward against the chute body 71. This makes it impossible to part the cover 72 from the chute body 71 without operating the knob 89.

With the above configuration of the chute 70, tablets of a predetermined number are dispensed from the tablet cassette 2 to the chute 70 based on the prescription data as well as the above described. In the chute 70, the gate plate 102 is positioned at the closed position and tablets dispensed from the tablet cassette 2 are stored in it. A user pushes the push-receiving portion 108 as the release member of the gate plate 102 into by the upper opening portion of the tablet container 6, so that the gate plate 102 is rotated from the closed position to the open position and the stored tablets are dispensed into the tablet container 6.

Figure 32:
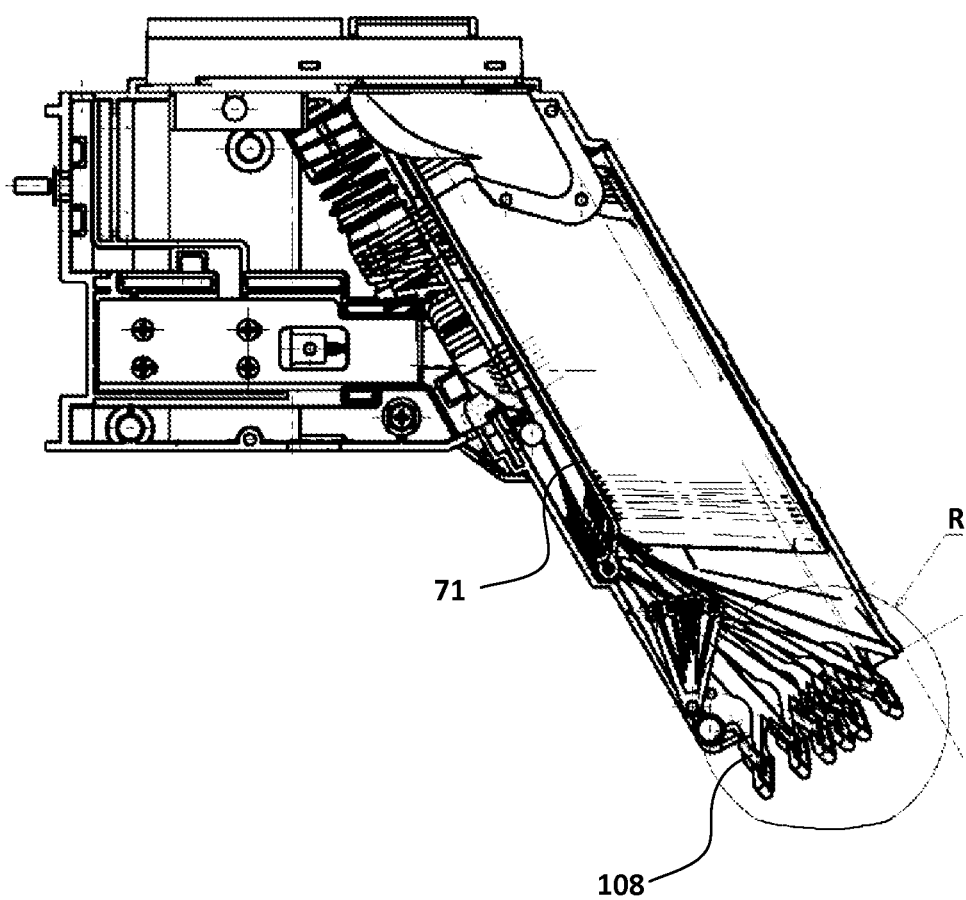
FIG. 32 shows a side view of the chute of FIG. 20 with the caver according to the first preferred embodiment.
Figure 33:
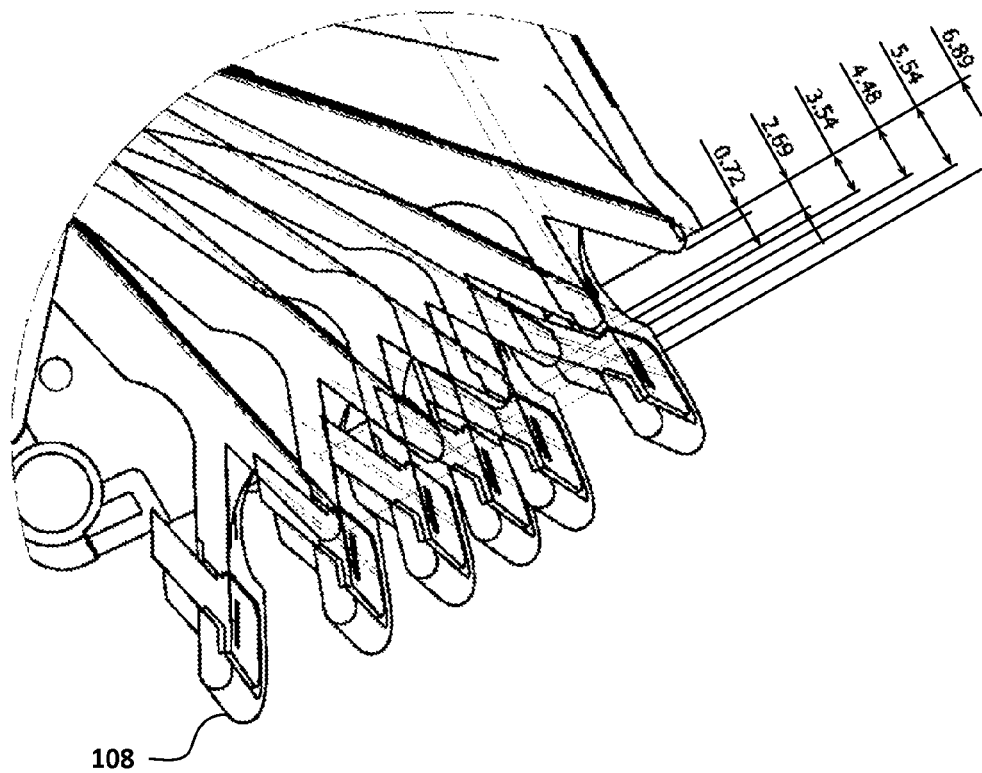
FIG. 33 shows an enlarged view of the moving illustration R in FIG. 32 according to the first preferred embodiment.

FIG. 32 shows a side view of the chute 2 of FIG. 20. The push-receiving portion 108, as the release member, moves from the staging portion to the dispensing position at least 5 mm in the direction of the tablet container 6 which is hold by a worker. Also, the gate plate 102, as the gate member, does not move perpendicularly relative to the chute 2. In FIG. 32, it is 0 mm at the time when the gate plate 102, as the gate member, is in closing position. FIG. 33 shows an enlarged view of the moving illustration R in FIG. 32. FIG. 33 shows opening movement of the push-receiving portion 108, as the release member, with six-staged illustrations (0.72 mm to 6.89 mm) where the opening movement is carried out by the worker to push the push-receiving portion 108 with the tablet container 6. In the maximum opening stage, the worker has to push the push-receiving portion 108, as the release member, strongly with the tablet container 6, which is hold by the worker so that wide open performance may be reached and the gate plate 102, as the gate member, can slide downward (6.89 mm) to open the gate member with maximum volume. By this configuration, the worker may get safety touch performance between the tablet container 6 and the push-receiving portion 108 which may prevent the drop of tablets. On the other hand, if the gate plate 102, as the gate member, would slant big downward, that makes a large chute body 71. This is mainly due to the fact that the gate plate 102, as the gate member, would have to be longer than the current embodiment, as shown in FIG. 32. Thus, it is enough to avoid an accident if the gate plate 102, as the gate member, would have moved at least 5 mm from the staging portion to the dispensing position in the direction of the tablet container 6, which is hold by the worker.

When using the chute 70, a fine powder from tablets may be attached to the interior surface. If the chute 70 is used for another kind of tablet, the problem of contamination may occur. As a result of this, it is needed to clean the chute 70. Thus, the cover 72 is removed from the chute body 71 and the attached fine powder is cleaned up. At this time, the knob 89 is operated and the locking piece 91 of the arm portion 90 is detached form the locking receiving wall 114 of the cover 72. This enables the cover 72 to detach from the chute body 71 by making the cover 72 slide downward against the chute body 71. The projecting portion 105 engages with the recess formed at the tip of the arm portion 90 and is positioned at the open position.

When the cover 72 is detached from the chute body 71, each of the engaging projecting portions 110, 111 is detached from each of the engaging holes 81, 88 respectively at a time. When the first engaging projecting portion 110 is detached from the first engaging hole 81, the rotating piece 83 loses the support of the first engaging projecting portion 110 and rotates according to the biasing force of the coil spring 84 and after, the locking projecting portion 86 locks the locking receiving portion 106 of the gate plate 102. This prevents the rotation of the gate plate 102 in addition to engagement of the recess 90a and the projecting portion 105, and functions as the second locking mechanism (so-called double lock mechanism). It is judged that the slide plate 93 is positioned at the upper position when the detected portion 98 is detected by the detection sensor 87. In this state, dispensing of tablets from the tablet cassette 2 is canceled based on the detection signal of the detection sensor 87.

When the cover is detached from the chute body 71, the place where the fine powder is attached is cleaned up by wiping and vacuuming, etc. Since it can be cleaned in the state that the cover 72 which occupies all of the front side of the chute 2 is detached, it is possible to clean all the area with good working efficiency.

When cleaning work is finished, the cover 72 is attached to the chute body 71. That is, the cover 72 is moved obliquely upward against the chute body 71, the shoulder 109 of the cover 72 is engaged with the receiving portion of the side of the tablet cassette 2 and each of the engaging projecting portions 110, 111 is inserted into each of the engaging holes 81, 88. When the first engaging projecting portion 110 is inserted into the first engaging hole 81, the rotating piece 83 is pushed into against the biasing force of the coil spring 99. Then, the locking projecting portion 86 is detached from the locking receiving portion 106 of the gate plate 102 and the slide plate 93 is rotated to the lower position by the biasing force of the coil spring 99. As a result, it is possible to dispense tablets from the tablet cassette 2 to the chute 70.

In addition, even if one comes into contact with the knob 89 by mistake during cleaning, the gate plate 102 is maintained in the opening position and is not rotated to the close position, since the locking projecting portion 86 of the rotating piece 83 is locked to the locking receiving portion 106. Thus, the detected portion 98 is not detected by the detection sensor 87, and dispensing tablets from the tablet cassette 2 is rejected.

In another possible configuration, two or more device bodies 1 are provided. In this case, the liquid crystal monitor 8 can be shared by two or more device bodies 1, and through touch operation of a screen switch button in the main screen as shown in FIG. 11, the screen may be switched to one showing the conditions of the tablet cassettes 2 of either of the device bodies 1.

In another possible configuration, the prescription number in the case that tablets are dispensed from the tablet dispenser and the result calculated on a monthly basis is displayed on the screen. Moreover, the detail of dispensing can be displayed on a daily basis, weekly basis and monthly basis, etc.

Although, in the third preferred embodiment, a solenoid (not shown) makes chute 3, 50, 70 be in the locking state and tablets are not dispensed without asking, a solenoid of each chute 3, 50, 70 can be freely controlled by the control unit 5. For example, it is possible to design such that the locking state of each chute 3, 50, 70 is cancelled individually or in line basis. It can be discriminated that the locking state is cancelled by changing the displaying configuration of the cassette column 41a displayed on the main screen 41. This enables the locking to be set arbitrarily for the chute 3, 50, 70 which it is desired to cancel, for example, in the case that each chute 3, 50, 70 is cleaned up, etc., and it becomes possible to respond according to user's needs.

Although, in the third preferred embodiment, dispensing tablets based on prescription data is performed in the input order without the case of setting the priority order, it may be possible to set the promised prescription time and to dispense tablets of the description having a long waiting time on a priority basis (promised prescription). That is, the promised prescription time (for example, 60 minutes) is set and if the promised prescription time goes through from the time receiving the prescription data, it is preferable to perform dispensing tablets based on the prescription in priority to another prescription. This enables to prevent the problem such as waiting for a long time with respect to a certain prescription.

Although, in the third preferred embodiment, when the demand of dispensing tablets is continued to the same tablet cassette 2 (waiting description), the number of the indicator displayed on the cassette column 41a of the main screen of the liquid crystal monitor 8 is changed, and the following configuration can be added.

That is, when the demand of dispensing tablets is continued to the same tablet cassette 2, if a barcode printed on a prescription is read by a barcode reader, it may be displayed on the liquid crystal panel 8 which prescription includes tablets dispensed to the chutes 3, 50, 70 at the moment.

For example, if the name of the tablets dispensed to the chutes 3, 50, 70 is not the same as the name of the tablets printed on the description, "the tablets are not dispensed" may be displayed on the liquid crystal panel 8. Moreover, the order of the prescription also may be displayed on it. That enables a user to confirm that the dispensed tablets correspond to which prescription. In addition, the case that the demand of dispensing tablets is continued corresponds to the case that a normal prescription, a promised prescription or a priority prescription is performed by itself or the combination of them is continued.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A dispensing chute assembly, comprising:
a first chute configured to receive objects to be dispensed, the first chute having an outlet;
a first passive dispensing unit attached to the chute outlet, the first passive dispensing unit having a staging portion, wherein objects are captured prior to dispensing, the staging portion including a gate member movable between a staging position, in which objects may be captured within the staging portion, and a dispensing position, in which the objects may be fed into a receptacle positioned below the first passive dispensing unit;
the first passive dispensing unit further including a release member, the release member being coupled with the gate member, such that movement of the release member from a staging position to a dispensing position moves the gate member from its staging position to its release position; and, a second dispensing unit located immediately below the first passive dispensing unit; the second dispensing unit having a second chute configured to receive objects to be dispensed;

wherein a lower portion of the first chute overlaps with an upper portion of a second chute positioned immediately below the first chute such that the second chute physically contacts and guides placement of a container into which tablets are dispensed from the first chute.

2. The chute assembly defined in claim 1, wherein the gate member includes a pin, and the release member includes a slot that receives the pin.

3. The chute assembly defined in claim 1, wherein the gate member can rotate about a pivot attached to the chute in a manner to be able to move upward and open a lower opening portion of the chute.

4. The chute assembly defined in claim 1, further comprising a spout positioned downstream of the staging portion.

5. The chute assembly defined in claim 4, wherein the spout is attached to the release member.

6. The chute assembly defined in claim 1, wherein the release member is coupled to the gate member such that gravity biases the release member toward the staging position.

7. A dispensing chute assembly, comprising:
a first chute configured to receive objects to be dispensed, the first chute having an outlet;
a first passive dispensing unit attached to the chute outlet, the first passive dispensing unit having a staging portion, wherein objects are captured prior to dispensing, the staging portion including a gate member movable between a staging position, in which objects may be captured within the staging portion, and a dispensing position, in which the objects may be fed via gravity into a receptacle positioned below the first passive dispensing unit;

the first passive dispensing unit further including a release member, the release member being coupled with the gate member, such that movement of the release member from a staging position to a dispensing position moves the gate member from its staging position to its release position;

a spout positioned downstream of the staging portion that is attached to the release member; and, a second dispensing unit located below the first passive dispensing unit; the second dispensing unit having a second chute overlapping the first chute; said second chute positioned to physically contact and guide placement of a container into which tablets are dispensed from the first chute.

8. The chute assembly defined in claim 7, wherein the gate member moves perpendicular relative to the chute as the gate member moves from the staging position to the dispensing position.

9. The chute assembly defined in claim 8, wherein the gate member includes a pin, and the release member includes a slot that receives the pin.

10. The chute assembly defined in claim 7, wherein the release member does not move in concert with the chute as the release member moves between the staging and dispensing positions.

11. The chute assembly defined in claim 7, wherein the release member is coupled to the gate member such that gravity biases the release member toward the staging position.

* * * * *